(12) United States Patent
Lin

(10) Patent No.: US 12,083,129 B2
(45) Date of Patent: *Sep. 10, 2024

(54) TREATMENT OF BREAST CANCER USING COMBINATION THERAPIES COMPRISING AN ATP COMPETITIVE AKT INHIBITOR, A CDK4/6 INHIBITOR, AND FULVESTRANT

(71) Applicant: Genentech, Inc., South San Francisco, CA (US)

(72) Inventor: Kui Lin, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

Patent file contains an affidavit/declaration under 37 CFR 1.130(b).

(21) Appl. No.: 18/101,377

(22) Filed: Jan. 25, 2023

(65) Prior Publication Data

US 2023/0330106 A1    Oct. 19, 2023

Related U.S. Application Data

(63) Continuation of application No. 16/989,528, filed on Aug. 10, 2020, now Pat. No. 11,576,919.

(60) Provisional application No. 62/935,526, filed on Nov. 14, 2019, provisional application No. 62/885,732, filed on Aug. 12, 2019.

(51) Int. Cl.
| | | |
|---|---|---|
| *A61K 31/566* | (2006.01) | |
| *A61K 31/138* | (2006.01) | |
| *A61K 31/517* | (2006.01) | |
| *A61K 31/519* | (2006.01) | |
| *A61K 9/00* | (2006.01) | |

(52) U.S. Cl.
CPC .......... *A61K 31/566* (2013.01); *A61K 31/517* (2013.01); *A61K 31/519* (2013.01); *A61K 9/0019* (2013.01); *A61K 31/138* (2013.01)

(58) Field of Classification Search
CPC ................ A61K 31/566; A61K 31/517; A61K 31/519; A61K 31/138
See application file for complete search history.

(56) References Cited

U.S. PATENT DOCUMENTS

| | | | |
|---|---|---|---|
| 11,576,919 B2 * | 2/2023 | Lin | A61P 35/04 |
| 2015/0258080 A1 | 9/2015 | Hager et al. | |
| 2017/0157124 A1 * | 6/2017 | Lin | A61K 31/437 |
| 2018/0055845 A1 | 3/2018 | Reents et al. | |
| 2021/0046086 A1 | 2/2021 | Lin | |

FOREIGN PATENT DOCUMENTS

| | | | | |
|---|---|---|---|---|
| WO | WO-2013173811 A1 | * | 11/2013 | .......... A61K 31/506 |
| WO | 2017161253 A1 | | 9/2017 | |
| WO | 2018233620 A1 | | 12/2018 | |
| WO | WO-2021/055517 A1 | | 3/2021 | |

OTHER PUBLICATIONS

Clinical trial NCT03959891. published online May 30, 2019 (Year: 2019).*
Jones (J. Clin. Oncology vol. 37 No. 15, abstract #1005, published online May 20, 2019). (Year: 2019).*
Cristofanilli (Lancet Oncology Vo. 17. pp. 425-439. Published 2016) (Year: 2016).*
Ippen (Neuro-Oncology vol. 21 pp. 1401-1411. Published online Jun. 7, 2019). (Year: 2019).*
International Search Report for PCT/EP2020/045584, mailed on Nov. 16, 2020.
clinicaltrials.gov. (Aug. 19, 2019) "A Study of Ipatasertib Plus Palbociclib and Fulvestrant Versus Placebo Plus Palbociclib and Fulvestrant in Hormone Receptor Positive and HER2 Negative Locally Advanced Unresectable or Metastatic Breast Cancer (IPATunity150)", Accession No. NCT04060862, 20 pages.
clinicaltrials.gov, (May 21, 2019) "AKT Inhibitor, Ipatasertib, With Endocrine and CDK 4/6 Inhibitor for Patients With Metastatic Breast Cancer (TAKTIC)", History of Changes for Study: NCT03959891, 20 pages.
Corte et al. (Oct. 1, 2016) "Ipatasertib (GDC-0068), A Novel Akt Inhibitor, Synergizes with Anti-microtubule Chemotherapic Agents in Human Breast Cancer Cell Lines", Annals of Oncology, 27(Suppl. 6): VI1-VI14 (1 page).
Cristofanilli et al. (Apr. 2016) "Fulvestrant plus palbociclib versus fulvestrant plus placebo for treatment of hormone-receptor-positive, HER2-negative metastatic breast cancer that progressed on previous endocrine therapy (PALOMA-3): final analysis of the multicentre, double-blind, phase", The Lancet Oncology, 17(4):425-439.
Ippen et al. (Nov. 2019) "Targeting the PI3K/Akt/mTOR pathway with the Pan-AKT inhibitor GDC-0068 in PIK3CA-mutant breast cancer brain metastases", Neuro-Oncology, 21(11):1401-1411.
Kwapisz et al. (Nov. 2017) "Cyclin-dependent Kinase 4/6 Inhibitors in Breast Cancer: Palbociclib, Ribociclib, and Abemaciclib", Breast Cancer Research and Treatment, 166(1):41-54 (7 pages).
Lin et al. (Apr. 1, 2013) "Targeting Activated AKT with GDC-0068, A Novel Selective AKT Inhibitor that is Efficacious in Multiple Tumor Models", Clinical Cancer Research, 19(7):1760-1772 (14 pages).

* cited by examiner

*Primary Examiner* — Clinton A Brooks
*Assistant Examiner* — George W Kosturko
(74) *Attorney, Agent, or Firm* — Mintz, Levin, Cohn, Ferris, Glovsky and Popeo, P.C.

(57) ABSTRACT

Provided herein are combination therapies comprising an ATP competitive AKT inhibitor, fulvestrant, and CDK4/6 inhibitor for use in treating hormone receptor positive and HER2 negative locally advanced unresectable or metastatic breast cancer.

19 Claims, 22 Drawing Sheets

FIG. 1A

| Cell line | Palbo IC50 (µM) | GDC0068 IC50 (µM) | ER WB | Her2 WB | PIK3CA | PTEN | EGFR | Braf |
|---|---|---|---|---|---|---|---|---|
| CAMA1 | 0.35 | 0.65 | 2 | 1 | . | F278fs,D92H | . | P41T |
| MDA-MB-415 | 10.00 | 0.65 | 1 | 1 | . | C136Y | R521K | P74A |
| T47D | 0.35 | 0.68 | 1 | 0 | H1047R | + | . | L646M |
| EFM-19 | 0.30 | 0.68 | 1 | 0 | H1047L | + | R521K | . |
| EFM-192A | 0.42 | 0.72 | 1 | 3 | C420R | + | . | . |
| MDA-MB-361 | 10.00 | 0.83 | 1 | 2 | E545K,K567R | + | T678M | . |
| MCF7 | 0.18 | 0.99 | 3 | 0 | E545K | + | . | . |
| ZR-75-1 | 2.19 | 1.00 | 1 | 2 | . | L108R | R521K | . |
| HCC712 | 1.37 | 1.27 | 3 | 1 | . | UNK | UNK | UNK |
| BT474 | 10.00 | 2.59 | 1 | 3 | K111N | + | . | . |
| HCC1419 | 2.92 | 4.64 | 1 | 3 | . | + | H988P | . |
| MDA-MB-175 | 7.59 | 6.27 | 2 | 2 | . | + | . | . |
| HCC2911 | 0.40 | 7.58 | 2 | 1 | E545K,D71TE | D268E | . | . |
| BT483 | 0.75 | 10.00 | 1 | 0 | E542K | + | . | . |
| HCC1428 | 2.15 | 10.00 | 3 | 0 | AMP | + | . | . |
| HCC1500 | 1.81 | 10.00 | 2 | 0 | AMP_UP | + | R521K | . |
| MDA-MB-134VI | 0.45 | 10.00 | 3 | 0 | D203E | A34D | R521K | . |
| SUM44PE | 0.23 | 10.00 | 3 | 0 | . | + | UNK | UNK |
| ZR-75-30 | 10.00 | 10.00 | 2 | 3 | I391M | + | R521K | I326T |

FIG. 1B

| KRAS | Akt1 | RB | CDK4 | CDK6 | p16,CDKN2A | p21,CDKN1A | Cyclin D1 | Cyclin E1 | p53 |
|---|---|---|---|---|---|---|---|---|---|
| . | . | . | . | . | . | S31R | AMP | T15N | P72R,R280T |
| . | . | . | . | DOWN | HEMIDEL | AMP | AMP | . | P72R |
| . | . | HEMIDEL | . | HEMIDEL | HEMIDEL | . | . | HEMIDEL | L194F |
| . | . | . | . | DOWN,HEMIDEL | HOMDEL | . | . | . | H193R |
| . | UP | . | . | . | . | . | AMP | . | P72R |
| . | D3N | . | . | HEMIDEL | D67H,HEMIDEL | . | AMP | HEMIDEL | E56*,P72R |
| . | . | Q736H,HEMIDEL | . | . | HOMDEL | . | . | . | P72R |
| UP | . | . | . | DOWN,HEMIDEL* | . | HEMIDEL | AMP | . | P72R |
| UNK | UNK | UNK | UNK | UNK | UNK | UNK | UNK | UNK | UNK |
| . | UP | HEMIDEL | . | . | HOMDEL | . | AMP | HEMIDEL | P72R,E285K |
| . | UP | HEMIDEL | . | HEMIDEL | HEMIDEL | . | . | . | P75R,Y220C |
| . | . | . | . | AMP | . | S31R | AMP | AMP | P72R |
| . | G478D | . | . | . | HOMDEL | F63L | AMP | D290N | P72R |
| . | . | . | . | . | HEMIDEL | S31R | HEMIDEL | . | . |
| . | UP | HEMIDEL | . | . | HEMIDEL | HEMIDEL | AMP | AMP | P72R,E285K |
| G12R,AMP | . | HEMIDEL | HEMIDEL | . | HOMDEL | HEMIDEL | AMP | . | . |
| G12R | UP | R661L,Q736K,HEMIDEL | . | DOWN | . | . | AMP | DOWN | P72R,E285K |
| UNK | UNK | UNK | UNK | UNK | UNK | UNK | UNK | UNK | UNK |
| . | UP | HEMIDEL | DOWN | HEMIDEL | HEMIDEL | . | . | . | P72R |

*FIG. 2A*

| Cell line | Palbo IC50 (µM) | GDC0068 IC50 (µM) | Bliss sum | Bliss pos. avg | Bliss max | HSA avg | ER WB |
|---|---|---|---|---|---|---|---|
| ZR-75-1 | 2.19 | 1.00 | 100.9 | 2.33 | 7.9 | 8.2 | 1 |
| BT483 | 0.75 | 10.00 | -168.3 | 0.60 | 6.1 | 8.0 | 1 |
| CAMA1 | 0.35 | 0.65 | 85.1 | 2.44 | 8.6 | 7.5 | 2 |
| T47D | 0.35 | 0.68 | -67.0 | 0.84 | 4.5 | 7.0 | 1 |
| MCF7 | 0.18 | 0.99 | -13.4 | 1.49 | 7.2 | 8.1 | 3 |
| BT474 | 10.00 | 2.59 | -70.5 | 1.31 | 8.0 | 8.0 | 1 |
| HCC1419 | 2.92 | 4.64 | -177.0 | 0.04 | 0.6 | 8.4 | 1 |
| HCC2911 | 0.40 | 7.58 | -88.0 | 0.82 | 4.0 | 4.7 | 2 |
| HCC712 | 1.37 | 1.27 | -257.0 | 0.21 | 0.9 | 4.6 | 3 |
| SUM44PE | 0.23 | 10.00 | -106.7 | 0.41 | 3.0 | 3.3 | 3 |
| MDA-MB-361 | 10.00 | 0.83 | -230.4 | 0.29 | 4.4 | 2.0 | 1 |
| EFM-192A | 0.42 | 0.72 | -397.6 | 0.02 | 0.0 | 1.6 | 1 |
| EFM-19 | 0.30 | 0.68 | -324.2 | 0.08 | 1.1 | 1.3 | 3 |
| HCC1428 | 2.15 | 10.00 | -42.0 | 0.63 | 2.9 | 1.2 | 3 |
| ZR-75-30 | 10.00 | 10.00 | -319.1 | 0.00 | -0.5 | 0.6 | 2 |
| MDA-MB-134VI | 0.45 | 10.00 | -94.8 | 0.25 | 1.8 | -0.8 | 3 |
| HCC1500 | 1.81 | 10.00 | -236.1 | 0.05 | 0.5 | -2.1 | 2 |
| MDA-MB-415 | 10.00 | 0.65 | -683.2 | 0.00 | -2.5 | -4.4 | 1 |
| MDA-MB-175 | 7.59 | 6.27 | -740.3 | 0.00 | -3.1 | -7.3 | 1 |

FIG. 2B

| Her2 WB | PIK3CA | PTEN | EGFR | RB | CDK4 | CDK6 | p16 CDKN2A | Cyclin D1 | Cyclin E1 |
|---|---|---|---|---|---|---|---|---|---|
| 2 | . | L108R | R521K | . | . | . | . | AMP | . |
| 0 | E542K | + | . | . | . | DOWN,HEMIDEL* | . | . | . |
| 1 | . | F278fs,D92H | . | . | . | . | HEMIDEL | HEMIDEL | T15N |
| 0 | H1047R | + | . | HEMIDEL | . | DOWN | HEMIDEL | AMP | . |
| 0 | E545K | + | . | Q736H,HEMIDEL | . | . | HOMDEL | . | HEMIDEL |
| 3 | K111N | + | . | HEMIDEL | . | . | HOMDEL | AMP | . |
| 3 | . | . | . | HEMIDEL | . | HEMIDEL | HEMIDEL | . | HEMIDEL |
| 1 | E545K,D717E | D268E | . | . | . | . | HOMDEL | AMP | D290N |
| 1 | . | UNK | UNK | UNK | UNK | UNK | UNK | UNK | UNK |
| 0 | . | + | UNK | UNK | UNK | UNK | UNK | UNK | UNK |
| 2 | E545K,K567R | + | T678M | . | . | HEMIDEL | D67H,HEMIDEL | AMP | HEMIDEL |
| 3 | C420R | + | . | . | . | . | HOMDEL | AMP | . |
| 0 | H1047L | + | R521K | . | . | DOWN,HEMIDEL | HOMDEL | . | . |
| 0 | AMP | + | . | HEMIDEL | . | HEMIDEL | HEMIDEL | . | AMP |
| 3 | I391M | + | R521K | HEMIDEL | DOWN | DOWN | . | AMP | DOWN |
| 0 | D203E | A34D | R521K | R661L,Q736K,HEMIDEL | HEMIDEL | . | . | AMP | . |
| 0 | AMP,UP | + | R521K | HEMIDEL | HEMIDEL | . | HOMDEL | AMP | . |
| 1 | . | C136Y | R521K | . | . | . | HEMIDEL | . | . |
| 2 | . | + | H988P | . | . | AMP | . | AMP | AMP |

TREATMENT OF BREAST CANCER USING COMBINATION THERAPIES COMPRISING AN ATP COMPETITIVE AKT INHIBITOR, A CDK4/6 INHIBITOR, AND FULVESTRANT

CROSS REFERENCE TO RELATED APPLICATIONS

This application is a continuation of U.S. application Ser. No. 16/989,528 filed Aug. 10, 2020, issued as U.S. Pat. No. 11,576,919, which claims the benefit of priority to U.S. Application No. 62/885,732 filed Aug. 12, 2019, and U.S. Application No. 62/935,526 filed Nov. 14, 2019, each of which is incorporated herein by reference in its entirety and for all purposes.

FIELD OF THE INVENTION

Provided herein are combination therapies comprising an ATP Competitive AKT inhibitor (e.g. ipatasertib or capivasertib); a CDK4/6 Inhibitor (e.g. palbociclib, ribociclib, or abemaciclib); and fulvestrant for the treatment of breast cancers.

BACKGROUND

Globally, breast cancer is the second most common invasive malignancy and the most common cause of cancer-related mortality in women, with a 5-year survival rate following metastatic diagnosis of approximately 15% (Jemal et al. 2011; Ferlay et al. 2015).

Accordingly, there is a pressing need for clinically active agents for treatment of Hormone Receptor Positive and HER2 Negative (HR+/HER2−) Locally Advanced Unresectable or Metastatic Breast Cancer.

SUMMARY

Provided herein are solutions to the problems above and other problems in the art.

In a first aspect provided herein is a combination therapy comprising an ATP competitive AKT inhibitor such as ipatasertib or capivasertib, a CDK4/6 inhibitor such as palbociclib, ribociclib, or abemaciclib, and fulvestrant.

In one aspect provided herein is a combination therapy comprising ipatasertib, palbociclib, and fulvestrant.

In another aspect provided herein is a combination therapy comprising an ATP competitive AKT inhibitor such as ipatasertib or capivasertib and a CDK4/6 inhibitor such as palbociclib, ribociclib, or abemaciclib.

In another aspect provided herein is a combination therapy comprising an ATP competitive AKT inhibitor such as ipatasertib or capivasertib and fulvestrant.

In a third aspect provided herein are methods of treating hormone receptor positive and HER2 negative locally advanced unresectable breast cancer by administering a combination therapy comprising ipatasertib, fulvestrant, and a CDK4/6 inhibitor (e.g. palbociclib, ribociclib, or abemaciclib).

In another aspect provided herein are methods of treating hormone receptor positive and HER2 negative locally advanced unresectable breast cancer by administering a combination therapy comprising ipatasertib and a CDK4/6 inhibitor (e.g. palbociclib, ribociclib, or abemaciclib).

In still another aspect provided herein are methods of treating hormone receptor positive and HER2 negative locally advanced unresectable breast cancer by administering a combination therapy comprising ipatasertib and fulvestrant.

In another aspect provided herein is a method of treating hormone receptor positive and HER2 negative locally advanced unresectable or metastatic breast cancer by administering a combination therapy comprising ipatasertib, palbociclib, and fulvestrant.

In still another aspect provided herein is a method of treating hormone receptor positive and HER2 negative locally advanced unresectable breast cancer by administering a combination therapy comprising ipatasertib, a CDK4/6 inhibitor (e.g. palbociclib), and fulvestrant by administering a combination therapy comprising a dosing regimen as set forth herein.

In yet another aspect provided herein is a method of treating hormone receptor positive and HER2 negative metastatic breast cancer (MBC) by administering a combination therapy comprising a dosing regimen as set forth herein.

In another aspect provided herein is use of a combination therapy comprising ipatasertib, fulvestrant, and a CDK4/6 inhibitor (e.g. palbociclib, ribociclib, or abemaciclib) in the manufacture of a medicament for treating hormone receptor positive and HER2 negative locally advanced unresectable breast cancer or metastatic breast cancer.

In another aspect provided herein is a combination therapy comprising ipatasertib, fulvestrant, and a CDK4/6 inhibitor (e.g. palbociclib, ribociclib, or abemaciclib) for use in the treatment of hormone receptor positive and HER2 negative locally advanced unresectable breast cancer or metastatic breast cancer.

In another aspect provided herein is use of a combination therapy comprising ipatasertib, fulvestrant, and palbociclib in the manufacture of a medicament for treating hormone receptor positive and HER2 negative locally advanced unresectable breast cancer or metastatic breast cancer.

In another aspect provided herein is a combination therapy comprising ipatasertib, fulvestrant, and palbociclib for use in the treatment of hormone receptor positive and HER2 negative locally advanced unresectable breast cancer or metastatic breast cancer.

In another aspect provided herein is use of a combination therapy comprising ipatasertib, fulvestrant, and a CDK4/6 inhibitor (e.g. palbociclib, ribociclib, or abemaciclib) and a dosing regimen as set forth herein in the manufacture of a medicament for treating hormone receptor positive and HER2 negative locally advanced unresectable breast cancer or metastatic breast cancer.

In another aspect provided herein is a combination therapy comprising ipatasertib, fulvestrant, and a CDK4/6 inhibitor (e.g. palbociclib, ribociclib, or abemaciclib) and a dosing regimen as set forth herein for use in the treatment of hormone receptor positive and HER2 negative locally advanced unresectable breast cancer or metastatic breast cancer.

In another aspect provided herein is a method of inhibiting tumor growth or producing/increasing tumor regression in a patient having hormone receptor positive and HER2 negative locally advanced unresectable BC or MBC by administering to the patient a combination therapy described herein according to the methods described herein.

In some embodiments, the cancer cells in a patient have a phosphatase and tensin homolog (PTEN) mutation, PTEN loss (or loss of function), a phosphatidylinositol-4,5-bisphosphate 3-kinase catalytic subunit alpha (PIK3CA) mutation, a protein kinase B alpha (AKT1) mutation, or a combination thereof, where such mutation can be determined using NGS.

The present embodiments can be understood more fully by reference to the detailed description and examples, which are intended to exemplify non-limiting embodiments.

BRIEF DESCRIPTION OF THE FIGURES

FIGS. 1A and 1B show breast cancer cell lines having differential single agent sensitivity to Ipatasertib and Palbociclib.

FIGS. 2A, 2B, 2C, and 2D show the combination effects between Ipatasertib and Palbociclib.

DETAILED DESCRIPTION

Figure 2C:
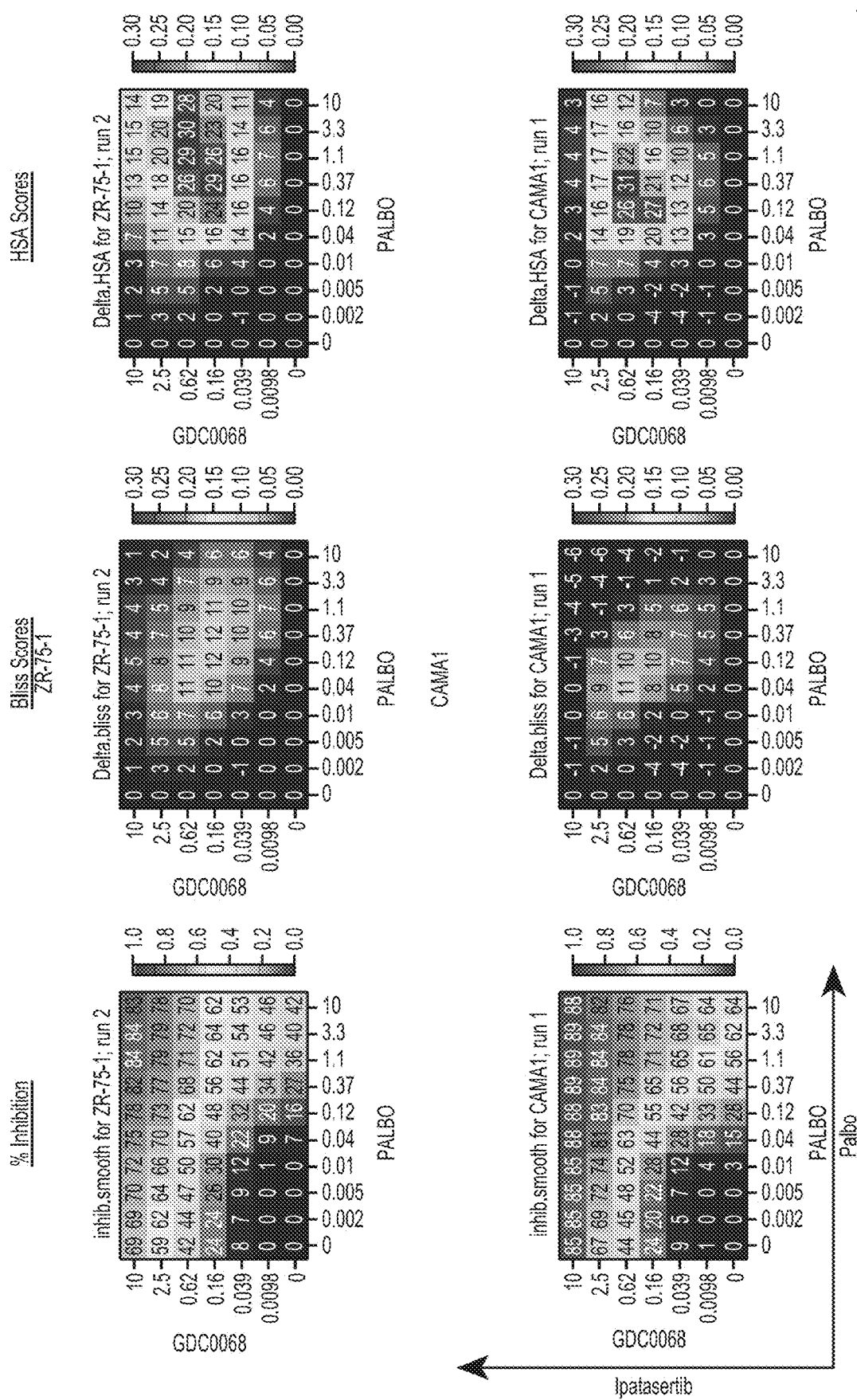
Figure 2D:
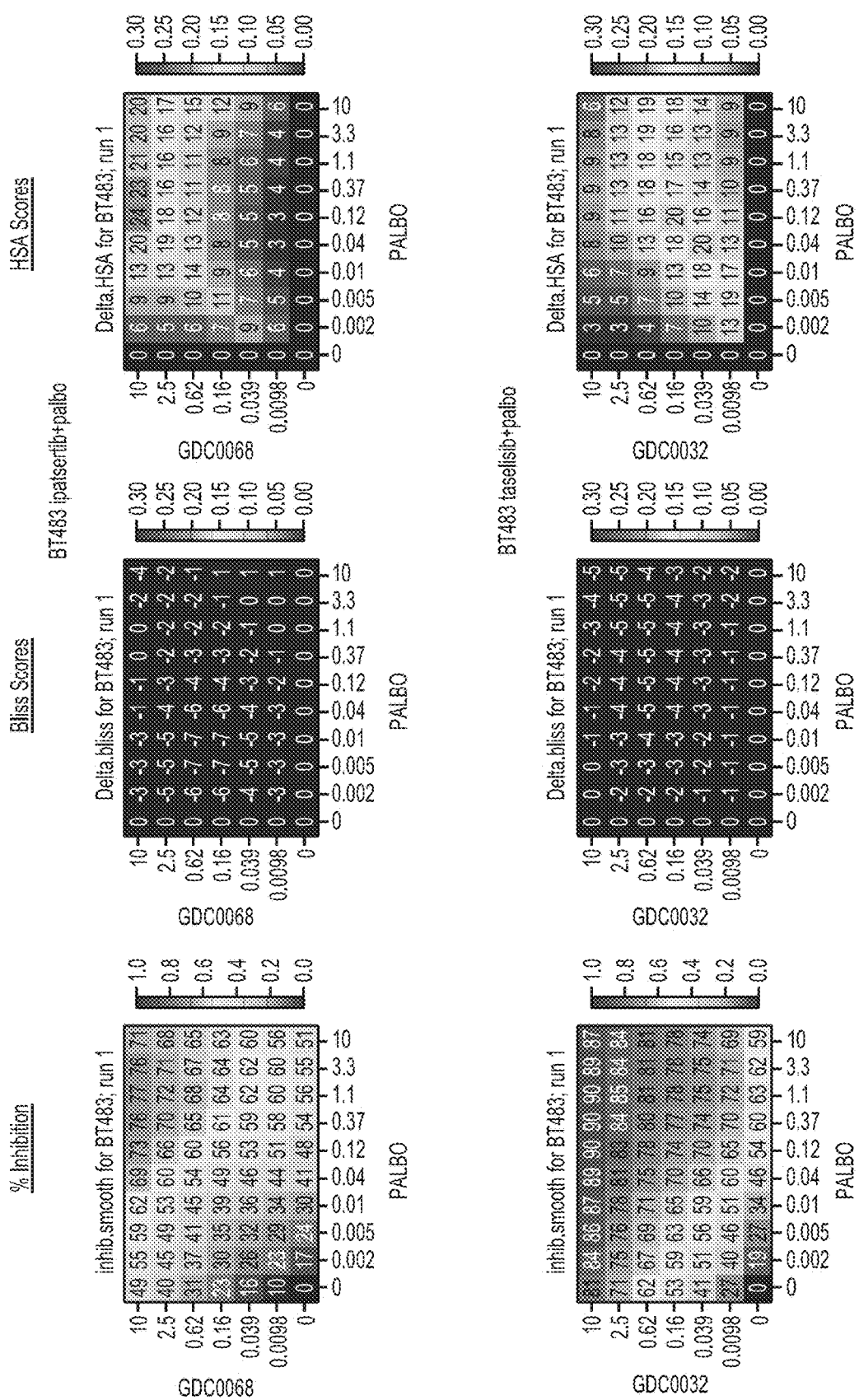
Figure 3A:
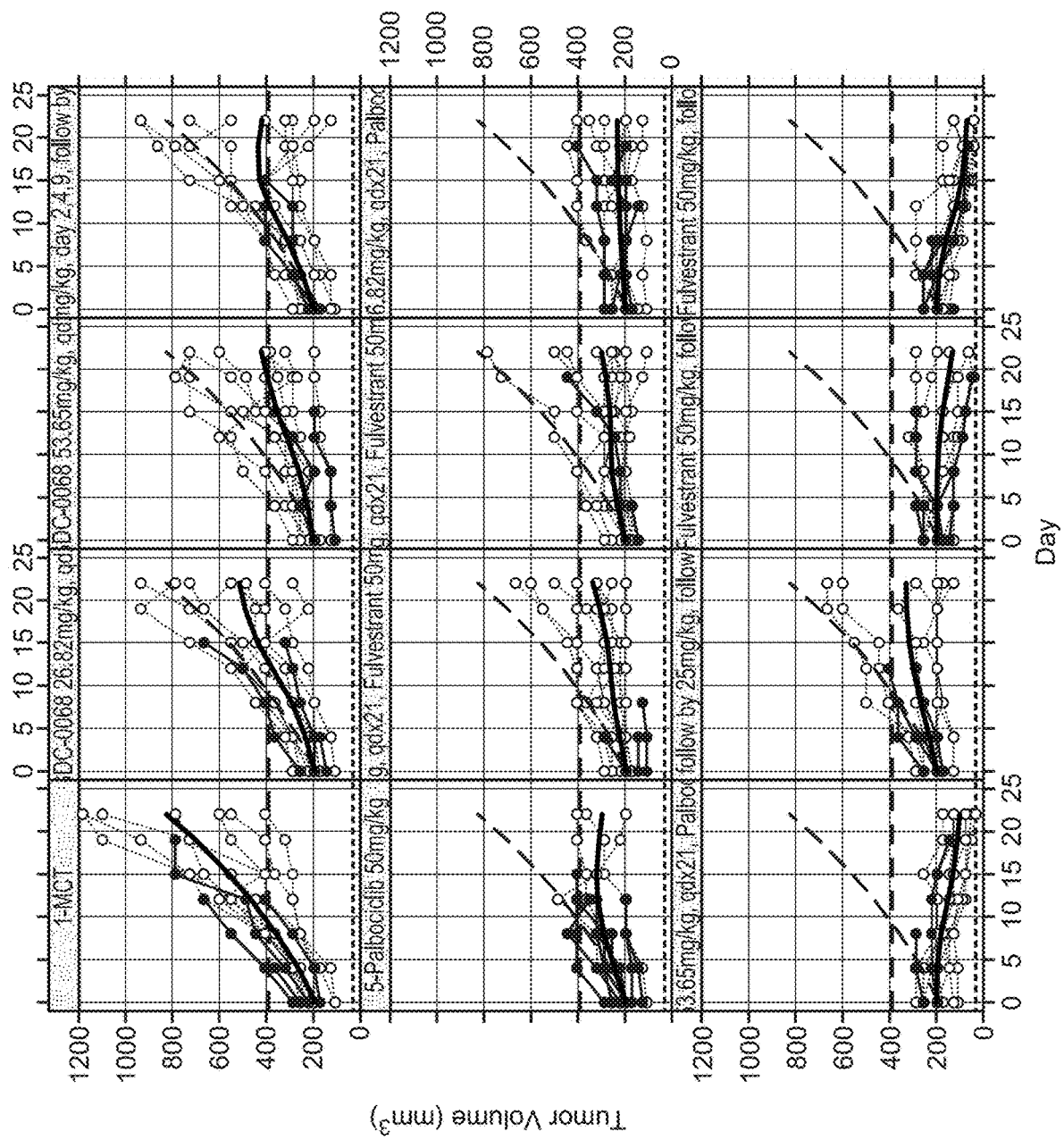
FIGS. 3A and 3B show the efficacy of Ipatasertib with Palbociclib and Fulvestrant in the MCF-7 (CRL) Breast Cancer Model.
Figure 3B:
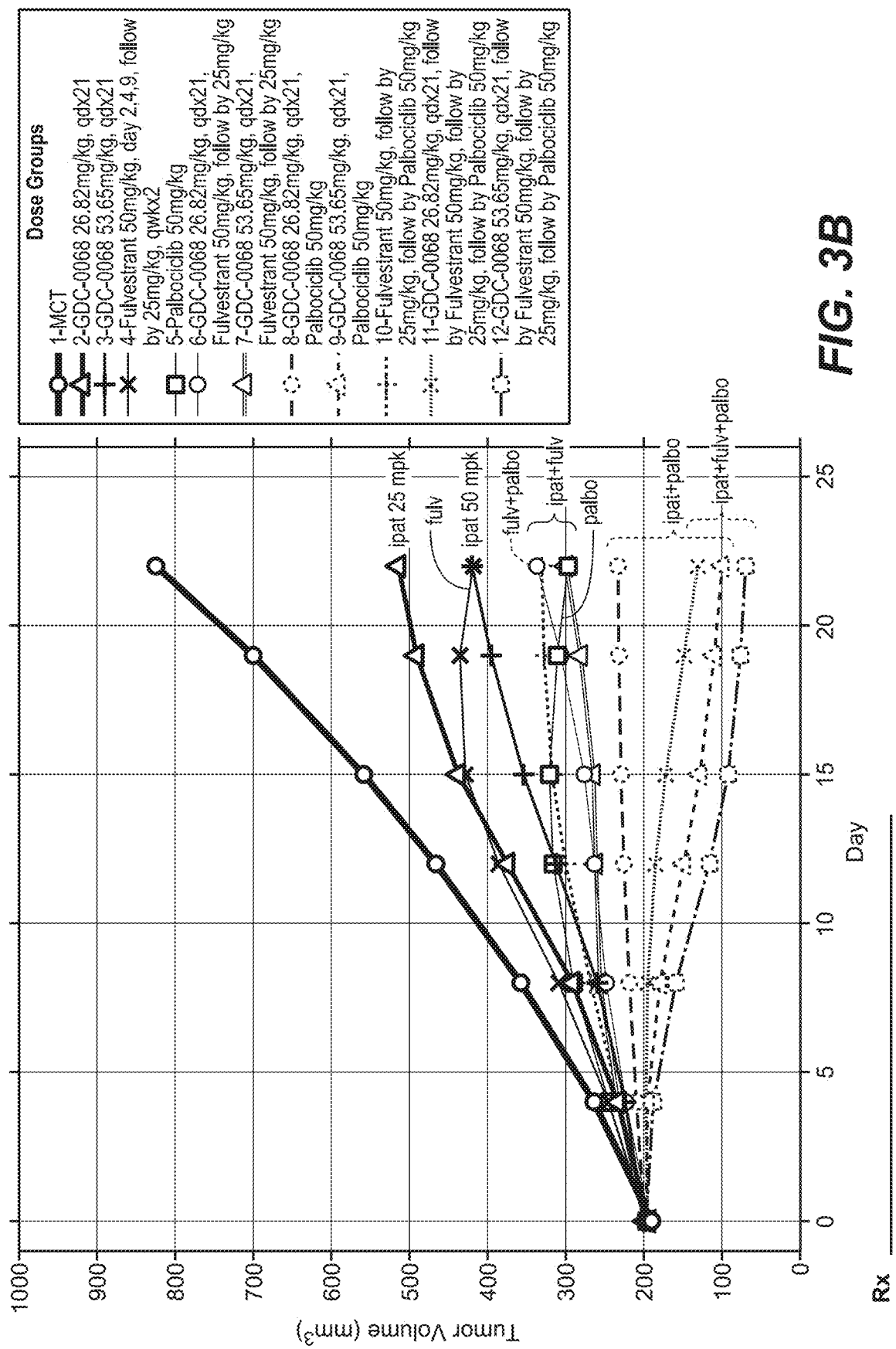
Figure 4A:
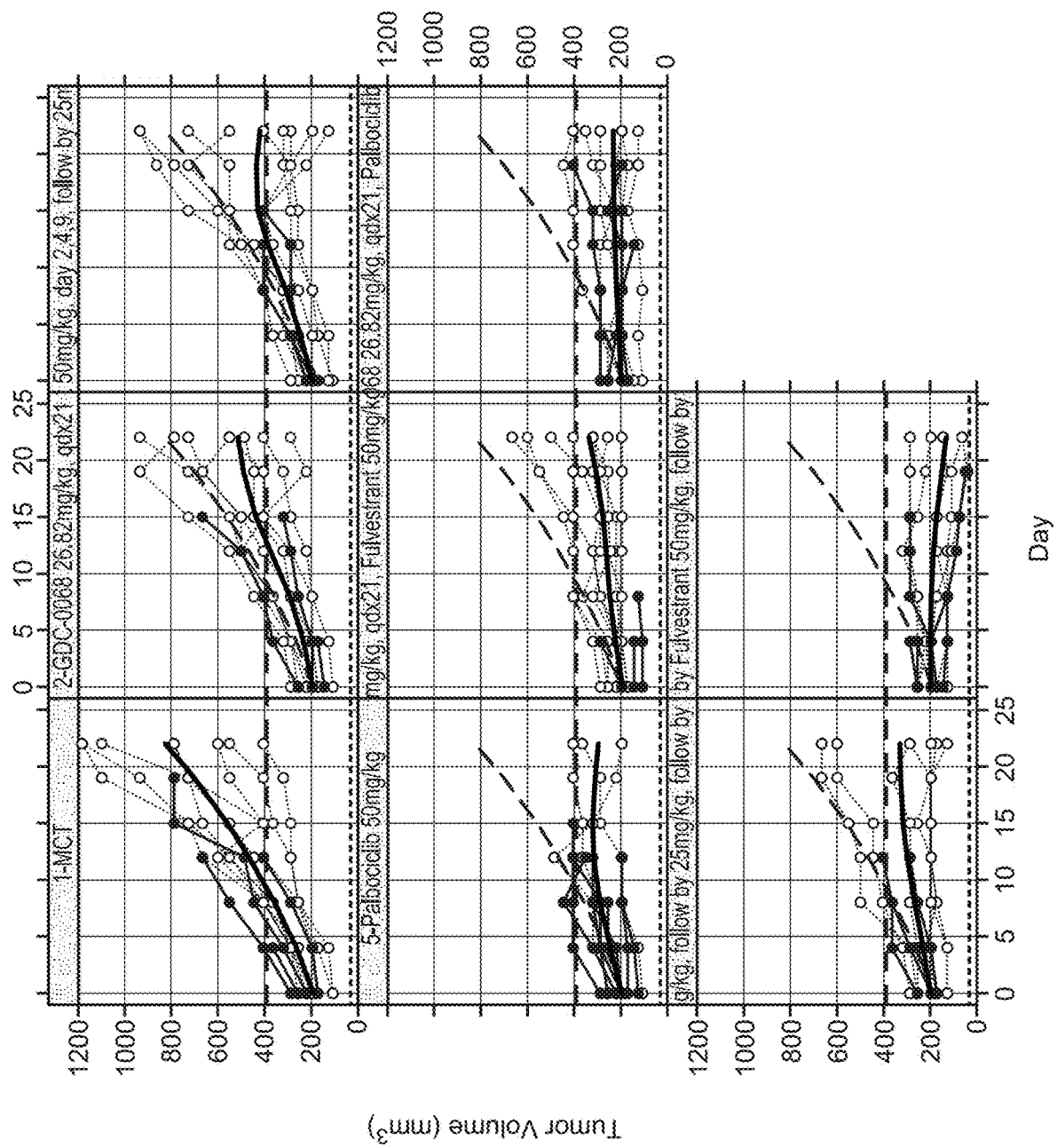
FIG. 4A and FIG. 4B show the efficacy of 25 mg/kg ipatasertib, ipatasertib and palbociclib, ipatasertib and fulvestrant, and ipatasertib/palbociclib/fulvestrant triple combination.
Figure 4B:
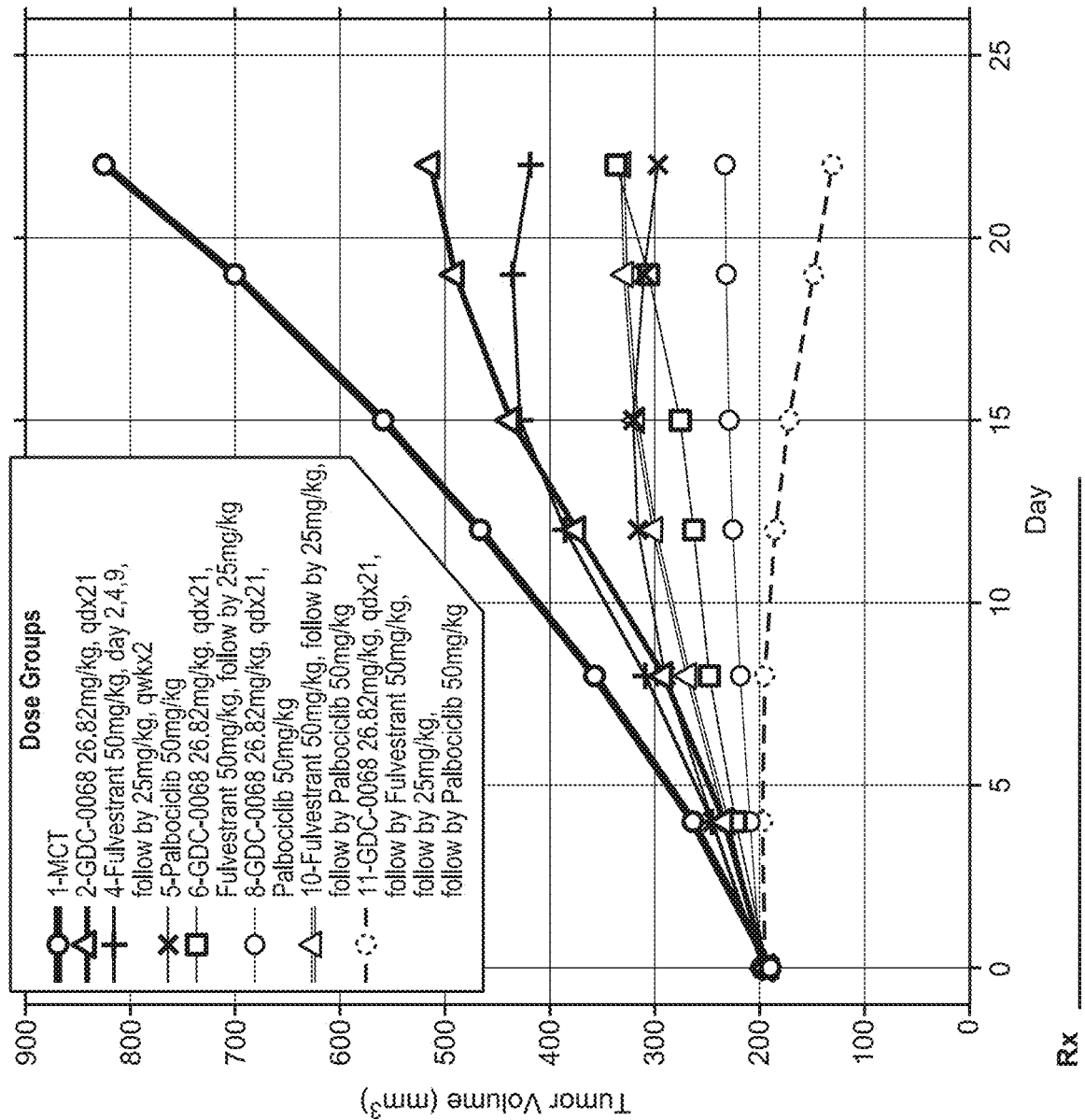
Figure 5A:
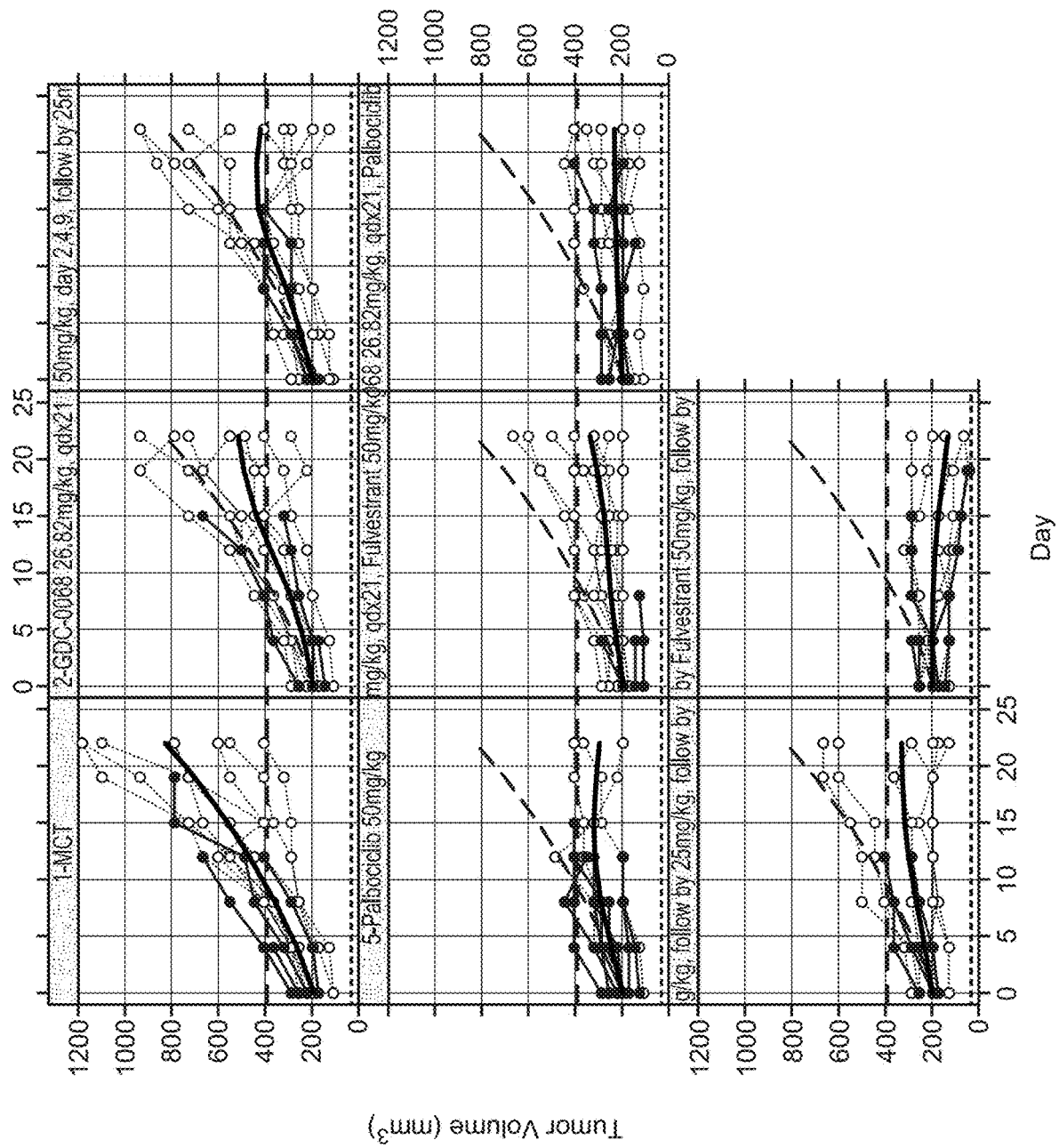
FIG. 5A and FIG. 5B show the efficacy of 50 mg/kg Ipatasertib with palbociclib and fulvestrant in the MCF-7 (CRL) Breast Cancer Model.
Figure 5B:
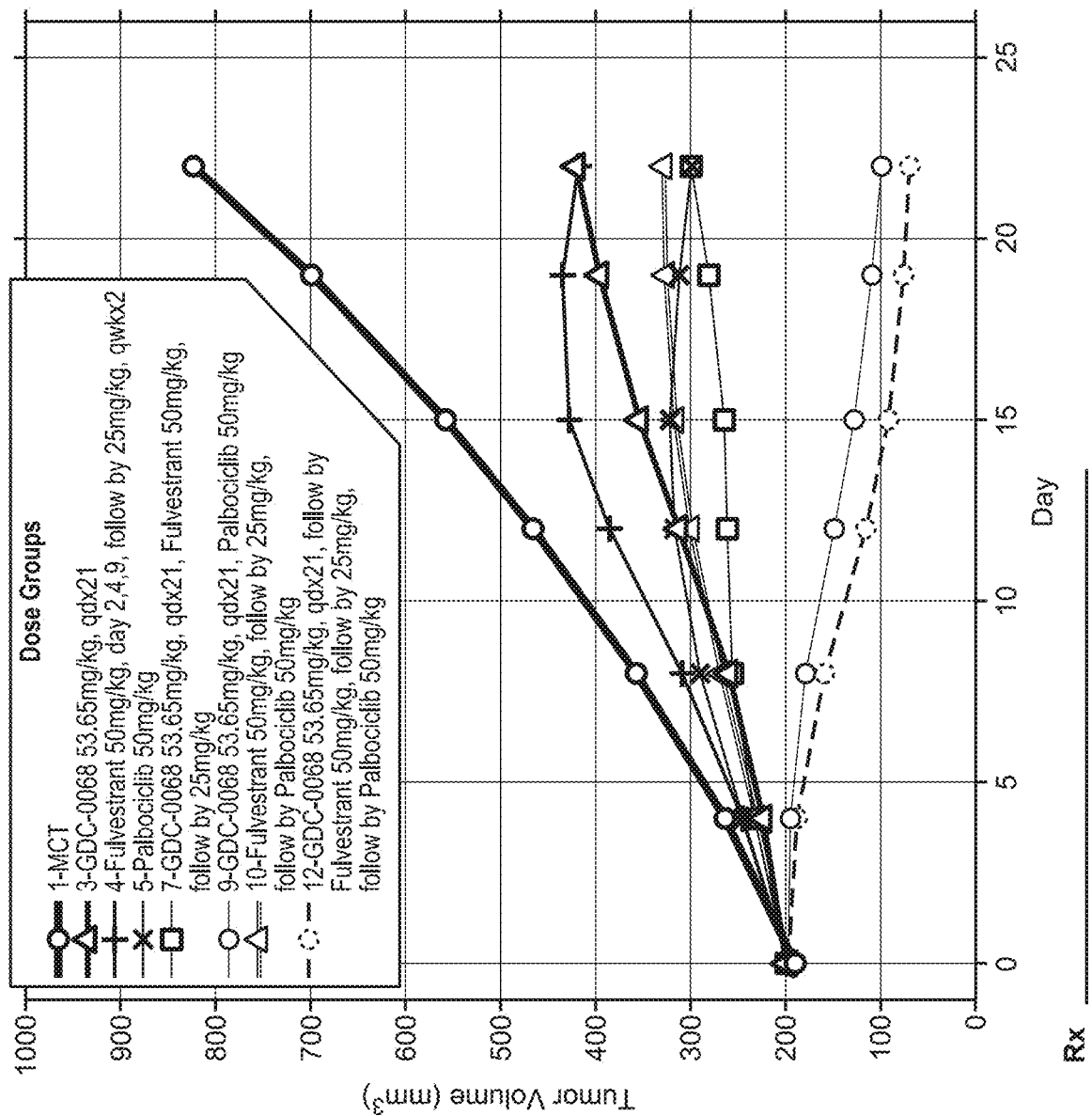
Figure 6A:
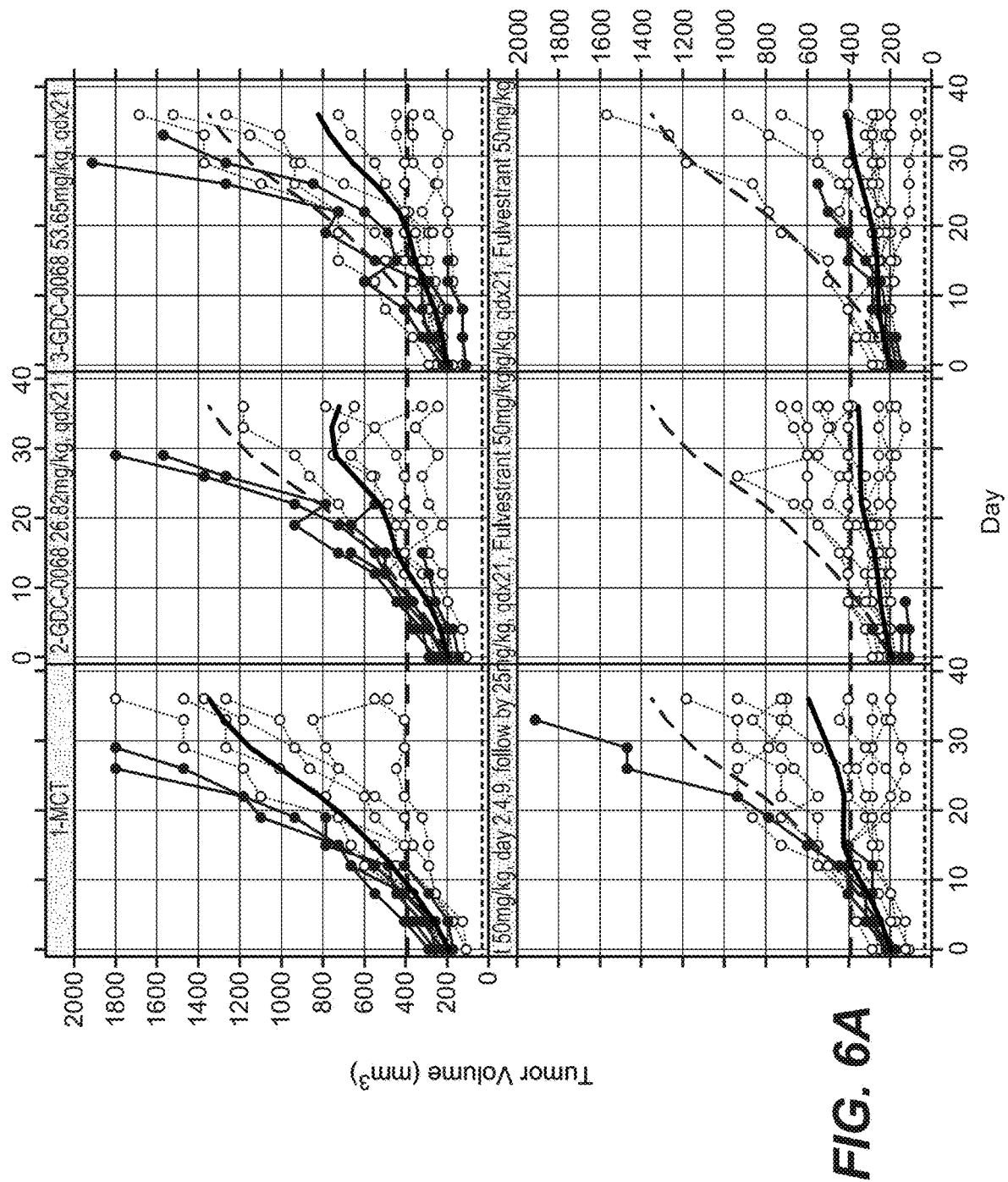
FIGS. 6A and 6B show the efficacy of 25 and 50 mg/kg ipatasertib and fulvestrant in combination.
Figure 6B:
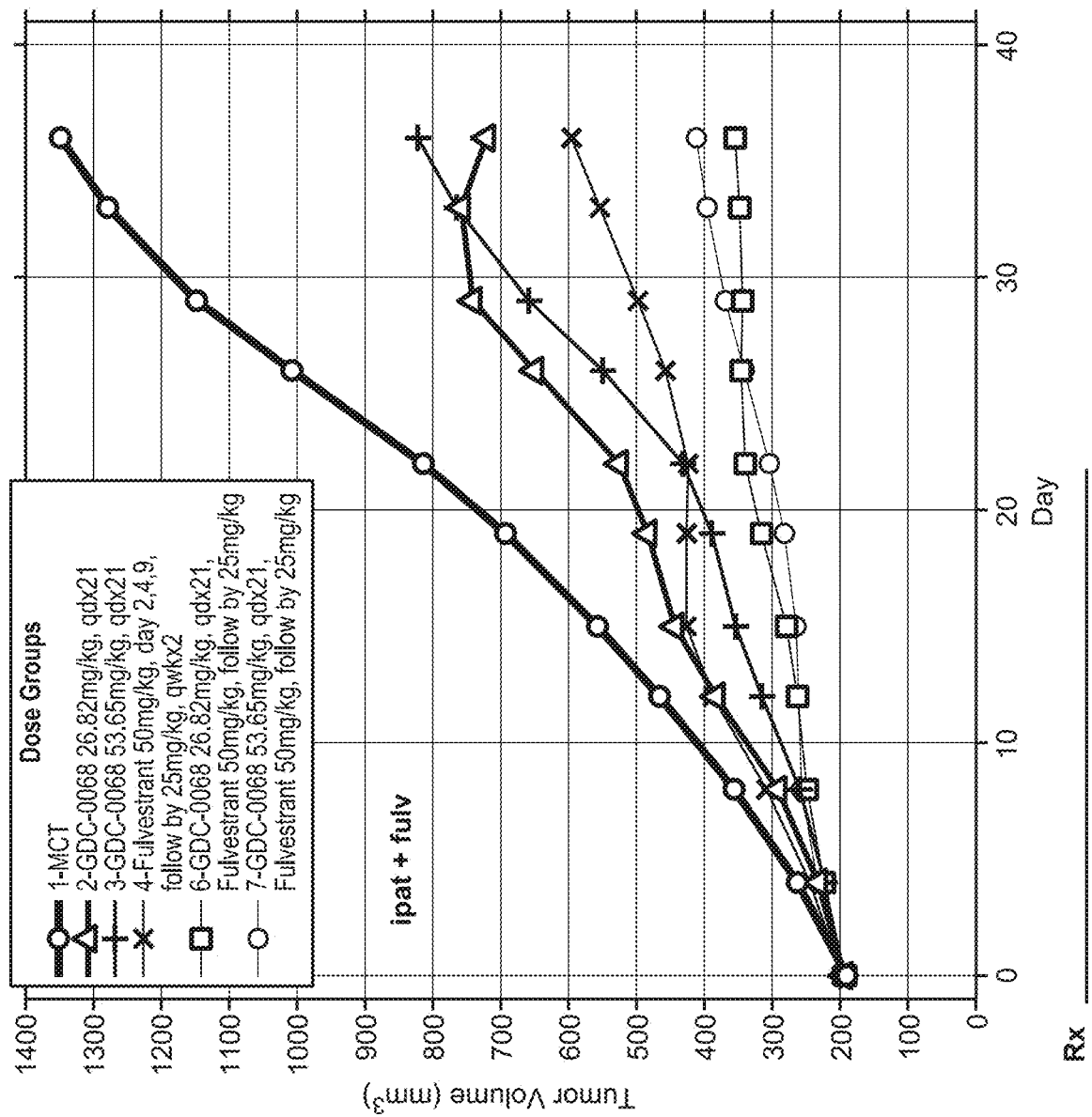
Figure 6C:
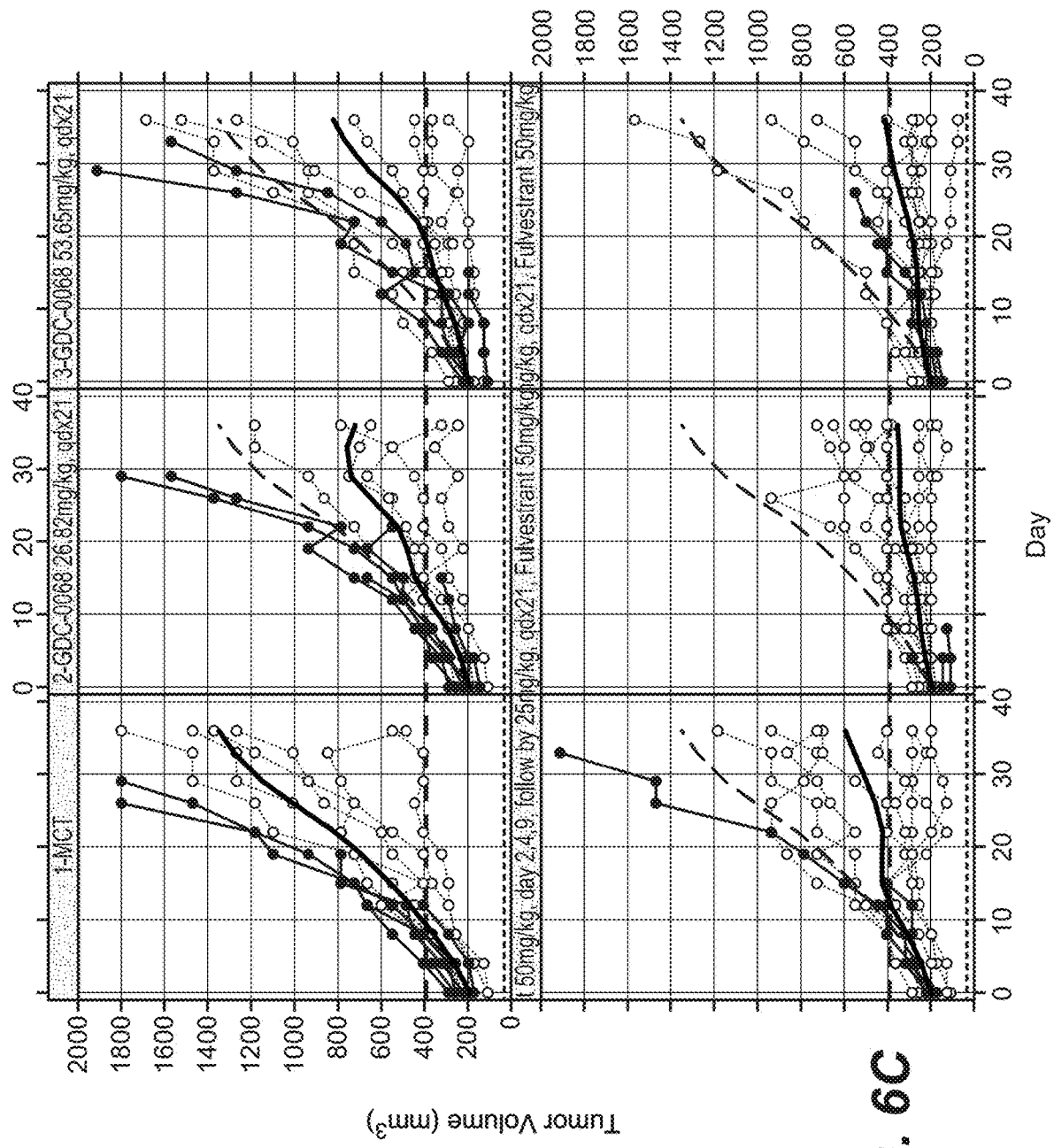
FIGS. 6C and 6D show the efficacy 25 and 50 mg/kg ipatasertib and palbociclib in combination.
Figure 6D:
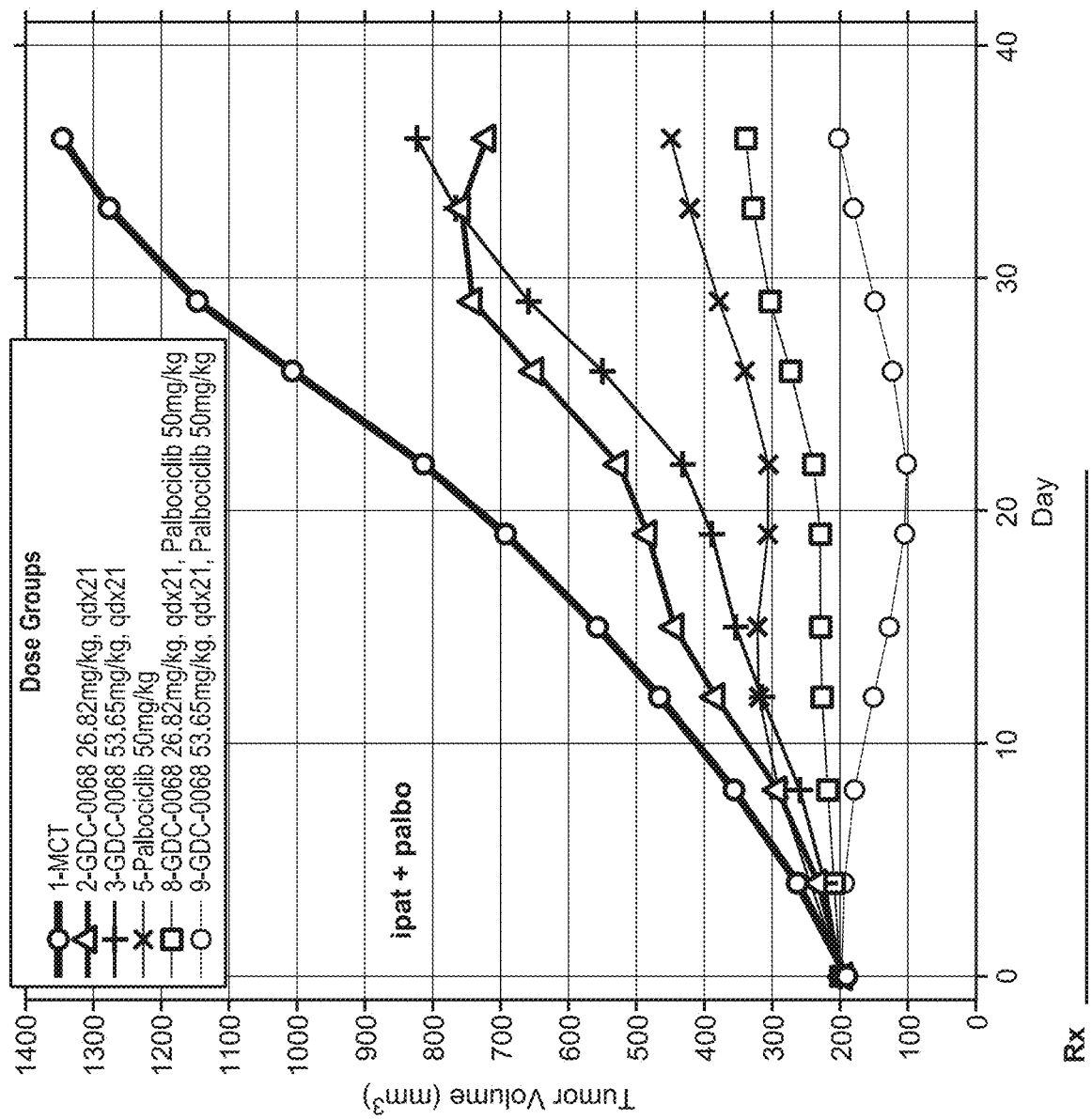
Figure 6E:
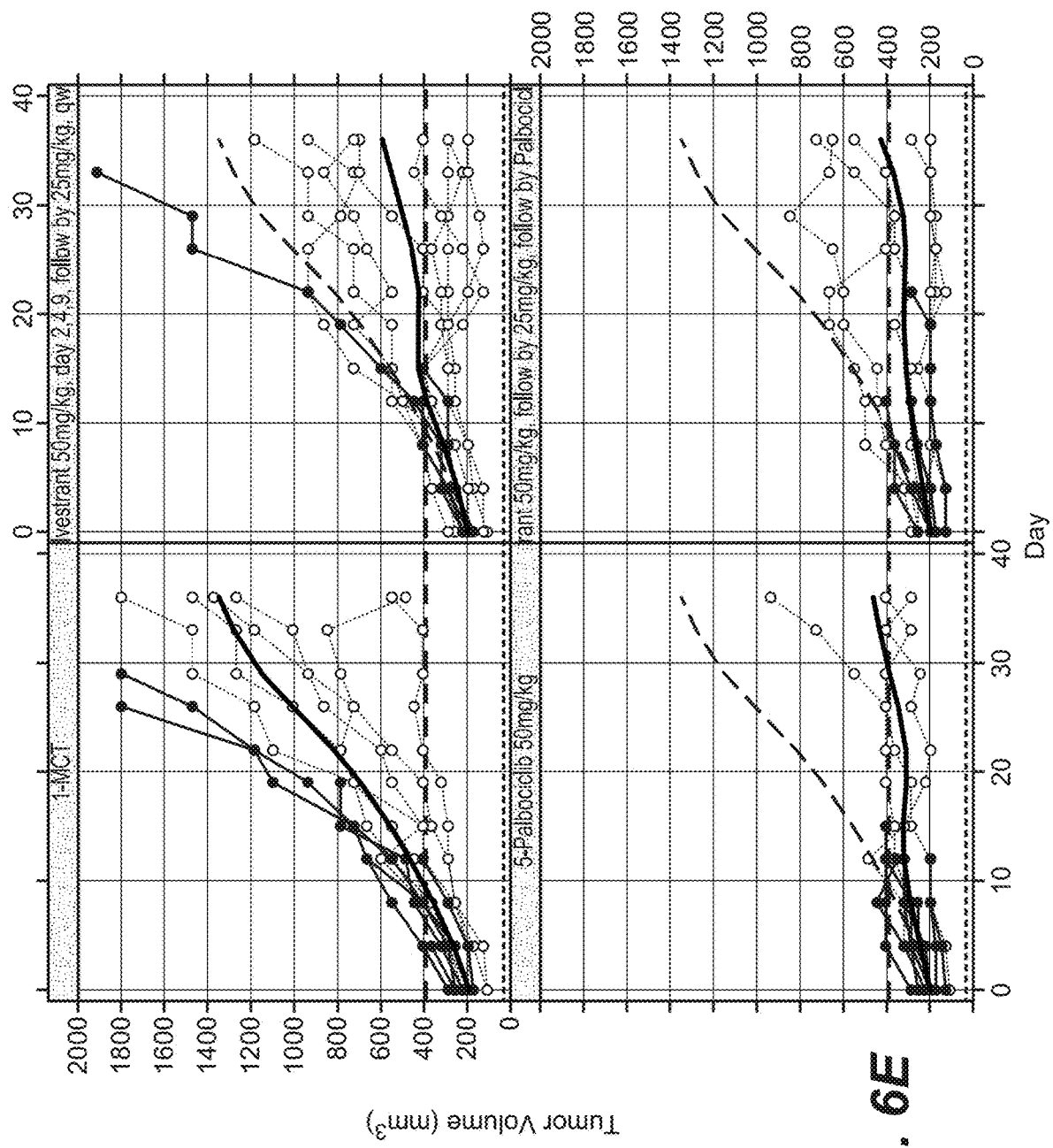
FIG. 6E and FIG. 6F show efficacy of palbociclib and fulvestrant monotherapy and in combination.shows.
Figure 6F:
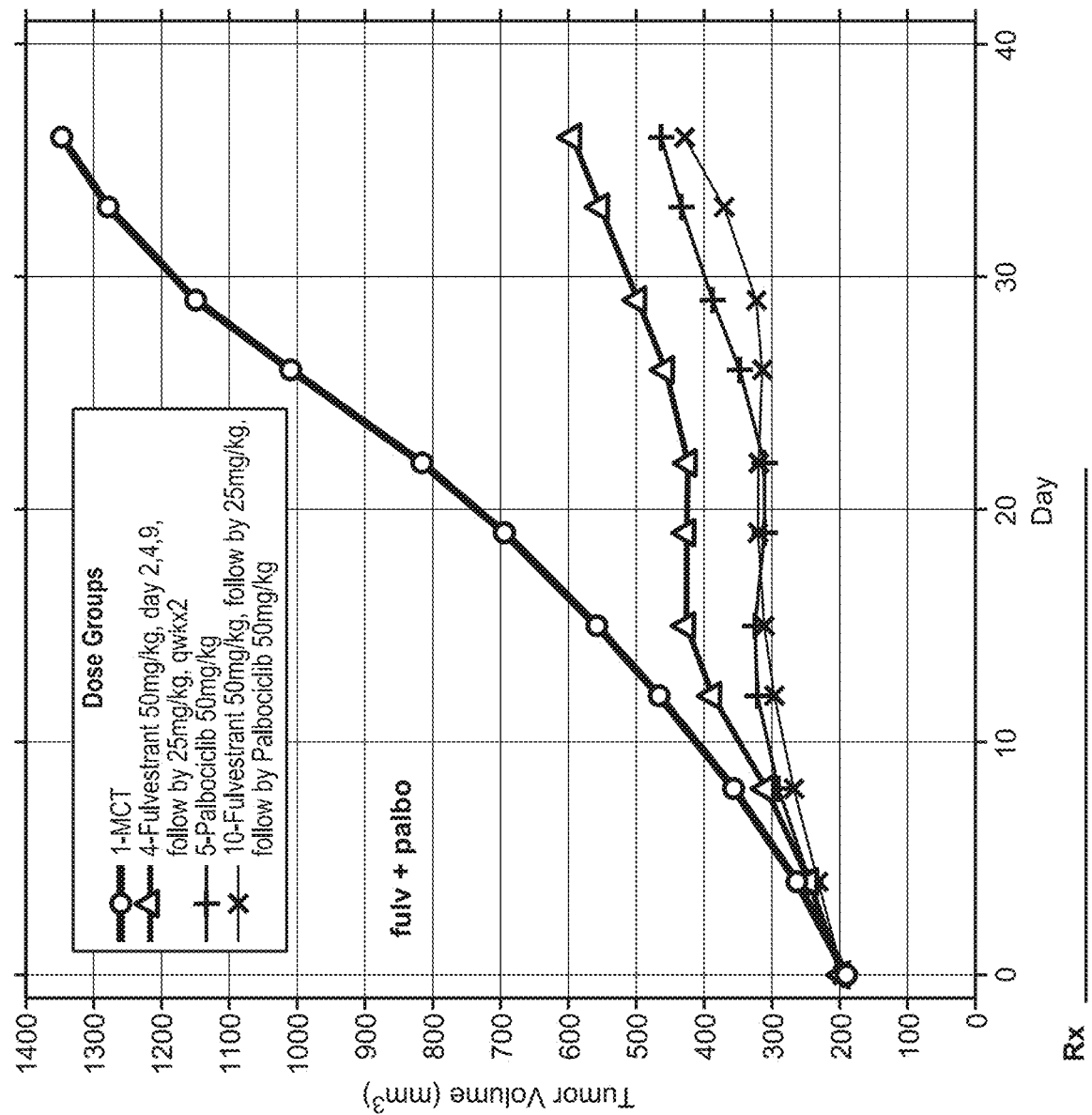

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

"Ipatasertib" refers to a compound having the structure:

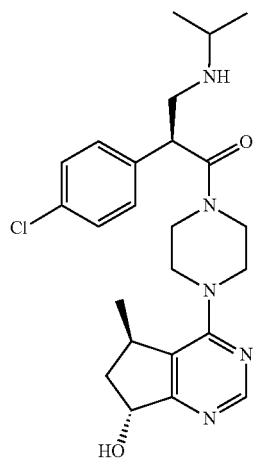 [SMILES: CC(C)NC[C@@H](C(=O)N1CCN(c2ncnc3c2[C@H](C)C[C@H]3O)CC1)c1ccc(Cl)cc1]

having the chemical name (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one. In one embodiment, ipatasertib is a monohydrochloride salt. In one embodiment, ipatasertib is an amorphous monohydrochloride salt.

"Palbociclib" refers to a compound having the structure:

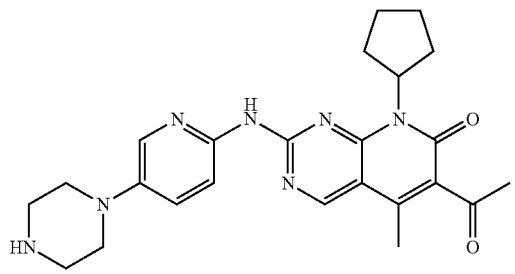 [SMILES: CC(=O)c1c(C)c2cnc(Nc3ccc(N4CCNCC4)cn3)nc2n(C2CCCC2)c1=O]

having the chemical name 6-acetyl-8-cyclopentyl-5-methyl-2-{[5-(piperazin-1-yl)pyridin-2-yl]amino}pyrido[2,3-d]pyrimidin-7(8H)-one. Palbociclib is marketed under the tradename IBRANCE®. Palbociclib is an exemplary "CDK4/6 inhibitor"—a class of agents targeting cyclin dependent kinase 4 and 6 (CDK4 and CDK6, respectively).

Other exemplary CDK4/6 inhibitors include, but are not limited to: ribociclib (Butanedioic acid—7-cyclopentyl-N,N-dimethyl-2-{[5-(piperazin-1-yl) pyridin-2-yl]amino}-7H-pyrrolo[2,3-d]pyrimidine-6-carboxamide (1/1); marketed as KISQALI®); abemaciclib, (2-Pyrimidinamine, N-[5-[(4-ethyl-1-piperazinyl)methyl]-2-pyridinyl]-5-fluoro-4-[4-fluoro-2-methyl-1-(1-methylethyl)-1H-benzimidazol-6-yl], marketed as VERZENIO®); and Trilaciclib (2'-((5-(4-methylpiperazin-1-yl)pyridin-2-yl)amino)-7',8'-dihydro-6'H-spiro(cyclohexane-1,9'-pyrazino(1',2':1,5)pyrrolo(2,3-d)pyrimidin)-6'-one).

"Fulvestrant" refers to a compound having the structure:

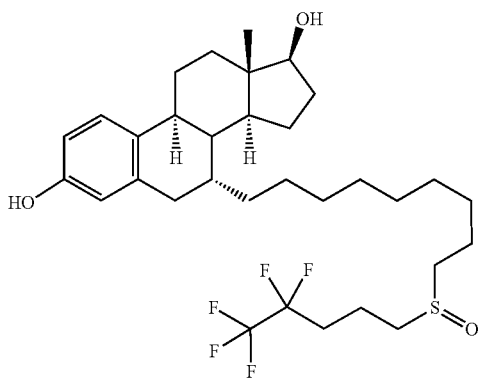

having the chemical name 7-alpha-[9-(4,4,5,5,5,-pentafluoropentylsulphinyl)nonyl]estra-1,3,5-(10)-triene-3,17-beta-diol. Fulvestrant is marketed under the tradename FASLODEX®.

"Overall survival" or "OS" refers to the time from enrollment to death from any cause.

"Objective response rate" or "ORR" refers the proportion of patients with a confirmed complete response or partial response on two consecutive occasions ≥4 weeks apart, as determined by the investigator according to RECIST v1.1.

"Time to progression" or "TTP" refers to the time from randomization until objective tumor progression.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

"Clinical benefit rate" or "CBR" refers to the proportion of patients with stable disease for at least 24 weeks or with confirmed complete or partial response, as determined by the investigator according to RECIST v1.1.

"Complete response" or "CR" refers to the disappearance of all target lesions and non-target lesions and (if applicable) normalization of tumor marker level.

"Partial response" or "non-CR/Non-PD" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

"Progressive disease" or "PD" refers to ≥20% increase in sum of diameters of target lesions, unequivocal progression in non-target lesions, and/or appearance of new lesions.

"Stable disease" or "SD" refers to neither sufficient shrinkage to qualify for CR or PR nor sufficient increase growth of tumor to qualify for PD.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a breast cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a breast cancer described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement or prevention of a breast cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. Thus, an "effective amount" may be considered in the context of administering one or more therapeutic agents, and a single agent may be considered to be given in an effective amount if, in conjunction with one or more other agents, a desirable result may be or is achieved.

An "administration period" or "cycle" refers to a period of time comprising administration of one or more agents described herein (i.e. ipatasertib, fulvestrant, and palbociclib) and an optional period of time comprising no administration of one or more of the agents described herein. For example, a cycle can be 28 days in total length and include administration of one or more agents for 21 days and a rest period of 7 days. A "rest period" refers to a period of time where at least one of the agents described herein (e.g. ipatasertib, fulvestrant, and palbociclib) are not administered. In one embodiment, a rest period refers to a period of time where none of the agents described herein (e.g. ipatasertib, fulvestrant, and palbociclib) are administered. A rest period as provided herein can in some instances include administration of another agent that is not ipatasertib, a CDK4/6 inhibitor (e.g. palbociclib), or fulvestrant. In such instances, administration of another agent during a rest period should not interfere or detriment administration of an agent described herein.

A "dosing regimen" refers to a period of administration of the agents described herein comprising one or more cycles, where each cycle can include administration of the agents described herein at different times or in different amounts.

"QD" refers to administration of a compound once daily.

A graded adverse event refers to the severity grading scale as established for by NCI CTCAE. In one embodiment, the adverse event is graded in accordance with the table below.

| Grade | Severity |
| --- | --- |
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living [a] |
| 3 | Severe or medically significant, but not immediately life-threatening; hospitalization or prolongation of hospitalization indicated; disabling; or limiting self-care activities of daily living [b, c] |
| 4 | Life-threatening consequences or urgent intervention indicated [d] |
| 5 | Death related to adverse event [d] |

Provided herein are combination therapies comprising an ATP competitive AKT inhibitor, fulvestrant, and a CDK4/6 inhibitor. In one embodiment is a combination therapy comprising ipatasertib, fulvestrant, and a CDK4/6 inhibitor. In another embodiment is a combination therapy comprising ipatasertib, fulvestrant, and palbociclib.

Further provided herein are combination therapies comprising an ATP competitive AKT inhibitor and one of fulvestrant or a CDK4/6 inhibitor. In one embodiment, such a combination therapy comprises ipatasertib and fulvestrant. In another embodiment, such a combination therapy comprises ipatasertib and a CDK4/6 inhibitor (e.g. palbociclib).

The combination therapies described herein can be provided as a kit comprising one or more of the agents for administration. In one embodiment, the kit includes ipatasertib and fulvestrant. In one embodiment, the kit includes ipatasertib and palbociclib. In another embodiment, the kit includes ipatasertib, fulvestrant, and palbociclib. In one embodiment, the agents of the combination therapy described herein are supplied in a kit in a form ready for administration or, for example, for reconstitution (e.g. for IV administration as described herein). Kits described herein can include instructions such as package inserts. In one embodiment, the instructions are package inserts—one for each agent in the kit.

Provided herein are methods of treating hormone receptor positive and HER2 negative locally advanced unresectable or metastatic breast cancer. In one embodiment, the method includes treating hormone receptor positive and HER2 negative (HR+ HER2−) locally advanced unresectable or metastatic breast cancer in a patient having hormone receptor positive and HER2 negative locally advanced unresectable or metastatic breast cancer by administering to the patient a combination therapy that includes ipatasertib, fulvestrant, and a CDK4/6 inhibitor such as palbociclib, ribociclib, or abemaciclib. In another embodiment is a method of treating hormone receptor positive and HER2 negative locally advanced unresectable or metastatic breast cancer in a patient having hormone receptor positive and HER2 negative locally advanced unresectable or metastatic breast cancer by administering to the patient a combination therapy that includes ipatasertib, fulvestrant, and palbociclib. In one embodiment, the patient has locally advanced unresectable or metastatic breast cancer and has relapsed during adjuvant endocrine therapy or has disease progression during the initial 12-months of 1L ("first line") endocrine therapy.

Further provided herein are methods of treating hormone receptor positive and HER2 negative locally advanced unresectable or metastatic breast cancer in a patient having hormone receptor positive and HER2 negative locally advanced unresectable or metastatic breast cancer by administering to the patient a combination therapy that includes ipatasertib and one of fulvestrant or a CDK4/6 inhibitor such as palbociclib, ribociclib, or abemaciclib. In one such embodiment, the methods comprise administering ipatasertib and fulvestrant as described herein. In another such embodiment, the methods comprise administering ipatasertib and palbociclib as described herein.

In one embodiment of the methods provided herein, the patient has locally advanced unresectable or metastatic breast cancer and has relapsed during adjuvant endocrine therapy or has disease progression during the initial 12-months of 1L ("first line") endocrine therapy.

In breast cancer, Akt appears to be one node along the PI3K/Akt pathway that controls apoptosis and cell growth (Yap T A, et al. Curr Opin Pharmacol 2008; 8:393-412), and this pathway is known to be activated in breast cancers. Up-regulation of Akt signaling (whether intrinsic or induced following chemotherapy) represents one potential survival pathway in response to genotoxic or mitotic stress. (Xu N, et al. J Oncol 2012; 2012:951724. doi: 10.1155/2012/951724.)

In one aspect provided herein is a method of treating hormone receptor positive and HER2 negative locally advanced unresectable or metastatic breast cancer in a patient having hormone receptor positive and HER2 negative locally advanced unresectable or metastatic breast cancer by administering to the patient a combination therapy comprising (i) an ATP competitive AKT inhibitor (e.g. ipatasertib or capivasertib); (ii) fulvestrant; and (iii) a CDK4/6 inhibitor (e.g. palbociclib, ribociclib, or abemaciclib), where the combination therapy is administered over a 28-day cycle.

In another aspect provided herein is a method of treating hormone receptor positive and HER2 negative locally advanced unresectable or metastatic breast cancer in a patient having hormone receptor positive and HER2 negative locally advanced unresectable or metastatic breast cancer by administering to the patient a combination therapy comprising an ATP competitive AKT inhibitor (e.g. ipatasertib or capivasertib) and one of either (x) fulvestrant or (y) a CDK4/6 inhibitor (e.g. palbociclib, ribociclib, or abemaciclib), where such a combination therapy is administered over a 28-day cycle.

In one aspect provided herein is a method of treating hormone receptor positive and HER2 negative locally advanced unresectable or metastatic breast cancer in a patient having hormone receptor positive and HER2 negative locally advanced unresectable or metastatic breast cancer by administering to the patient a combination therapy comprising (i) ipatasertib; (ii) fulvestrant; and (iii) a CDK4/6 inhibitor (e.g. palbociclib, ribociclib, or abemaciclib), where the combination therapy is administered over a 28-day cycle.

In one embodiment, the method includes a combination therapy comprising (i) ipatasertib; (ii) fulvestrant; and (iii) palbociclib. In one embodiment, the method includes a combination therapy comprising (i) ipatasertib; (ii) fulvestrant; and (iii) palbociclib administered in accordance with a dosing regimen described herein.

In another aspect provided herein is a method of treating hormone receptor positive and HER2 negative locally advanced unresectable or metastatic breast cancer in a patient having hormone receptor positive and HER2 negative locally advanced unresectable or metastatic breast cancer by administering to the patient a combination therapy comprising ipatasertib and one of either (x) fulvestrant or (y) a CDK4/6 inhibitor (e.g. palbociclib, ribociclib, or abemaciclib), where the combination therapy is administered over a 28-day cycle.

In one such embodiment, the method includes a combination therapy comprising ipatasertib and one of either (x) fulvestrant or (y) palbociclib. In one embodiment, the method includes a combination therapy comprising ipatasertib and one of either (x) fulvestrant or (y) palbociclib administered in accordance with a dosing regimen described herein.

Agents described herein can be administered in accordance with a package insert. In one embodiment of the methods described herein, agents can be administered in an effective amount as described herein. In one embodiment of the methods described herein, ipatasertib is administered orally at an amount of 300 mg. Such administration can be in a single dose (i.e. a single or multiple pills). In one embodiment, the dose of ipatasertib is 400 mg or 200 mg or 100 mg. Ipatasertib can be administered orally QD as described herein. In another embodiment, ipatasertib is administered in a dosing regimen as described herein.

In another embodiment, ipatasertib is administered as a single agent at least 1, 2, 3, 4, 5, 6, 7, 8, 9, or 10 days prior to administering any other agent in the combination therapy described herein (e.g. fulvestrant or palbociclib). In one such embodiment, ipatasertib is administered QD for an initial 5-7 days (a "run in period") prior to administration of another agent in the combination therapy described herein. Following the run in period, ipatasertib is administered in accordance with a dosing regimen set forth herein. In one such embodiment, following the run in period, ipatasertib is administered on days 1-21 of each 28-day cycle provided herein.

In one embodiment of the methods described herein, administration of ipatasertib occurs before IV infusion of another agent (e.g. fulvestrant). In one embodiment of the methods described herein, administration of ipatasertib occurs before administration of fulvestrant and the administration of fulvestrant occurs before the administration of a CDK4/6 inhibitor (e.g. palbociclib). In another embodiment, ipatasertib is administered prior to or concurrently with palbociclib and fulvestrant is administered thereafter.

In one embodiment, patients are tested for the presence, level, or amount of a compound having structure:

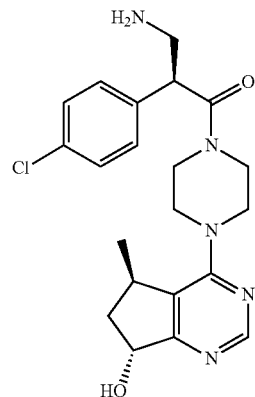 [SMILES: C[C@@H]1C[C@@H](O)c2ncnc(N3CCN(C(=O)[C@H](CN)c4ccc(Cl)cc4)CC3)c21]

having the chemical name, (S)-3-amino-2-(4-chlorophenyl)-1-(4-((5R,7R)-7-hydroxy-5-methyl-6,7-dihydro-5H-cyclopenta[d]pyrimidin-4-yl)piperazin-1-yl)propan-1-one, which is a metabolite of ipatasertib.

In another embodiment of the methods described herein, fulvestrant is administered at a dose of about 500 mg. In one embodiment of the methods described herein, fulvestrant is administered in accordance with a package insert. In one embodiment, fulvestrant is administered as two separate 250 mg intramuscular injections. In another embodiment, fulvestrant is administered in a dosing regimen as described herein. In one such embodiment, fulvestrant is administered on days 1 and 15 of the first 28-day cycle and on day 1 of each subsequent 28-day cycle thereafter.

In one embodiment of the methods described herein, palbociclib is administered as an agent of the triple combination therapy described herein. In one embodiment, palbociclib is administered orally at an amount of 125 mg, 100 mg, or 75 mg. In another embodiment, palbociclib is administered orally at an amount of 125 mg. In another embodiment, palbociclib is administered orally at an amount of 100 mg. In still another embodiment, palbociclib is administered orally at an amount of 75 mg. Is such embodiments, palbociclib is administered QD on days 1-21 of each 28-day cycle. In another embodiment of the methods described herein, palbociclib is administered in accordance with a package insert. In one embodiment, palbociclib is administered orally QD on days 1-21 of each 28-day cycle at an amount described herein. In still another embodiment, the amount of palbociclib is modified (e.g. reduced) from the initial dosage. In one such embodiment, the amount of palbociclib administered is reduced from 125 mg to 100 mg and can be, in one embodiment, further reduced to 75 mg. In another embodiment, palbociclib is administered in a dosing regimen as described herein.

In one embodiment, the methods described herein include a combination therapy described herein administered according to a dosing regimen comprising one 28-day cycle. In one embodiment, the first 28-day cycle is preceded by a 5-7 day run in dosage with ipatasertib as provided herein. In another embodiment, the methods described herein include a combination therapy described herein administered according to a dosing regimen comprising a first 28-day cycle followed by 2-10 28-day cycles. In still another embodiment, the methods described herein include a combination therapy described herein administered according to a dosing regimen comprising a first 28-day cycle followed by 2-8 28-day cycles. In one embodiment of the methods described herein, the dosing regimen comprises a first 28-day cycle followed by 2-24, 2-18, 2-12, 2-10, 2-8, 2-6, or 2-4 28-day cycles.

Further embodiments of the methods of treating hormone receptor positive and HER2 negative locally advanced unresectable or metastatic breast cancer are provided herein.

In one embodiment, the efficacy of the combination is measured as a function of PFS. In one such embodiment, PFS of the patient is increased by 3, 4, 5, 6, 7, 8, 9, 10, 15, 20, or more months compared to non-treatment or SOC treatment. In one embodiment, PFS is measured for at least 64 months following the first dosage of the combination therapy described herein. In another embodiment, the efficacy is measured as a function of PFS in a biomarker positive patient set (e.g. a biomarker panel as described herein including PIK3CA/AKT1/PTEN) comparable to a biomarker negative patient set.

In one embodiment, treatment with a combination therapy according to the methods provided herein increases a patient's OS by 3, 4, 5, 6, 7, 8, 9, 10, 15, 20 or more months comparable to non-treatment or SOC treatment. In one embodiment, treatment with a combination therapy according to the methods provided herein increases the patient's amount of ORR. In another embodiment, efficacy of response is measured as a function of DOR comparable to non-treatment or SOC treatment. In still another embodiment, efficacy of response is measured as a function of CBR comparable to non-treatment or SOC treatment.

In another embodiment, the TTP is increased in a patient following treatment with a combination therapy according to the methods provided herein. In another embodiment, the PFS is increased in a patient following treatment with a combination therapy according to the methods provided herein. In one embodiment provided herein a patient is diagnosed having a CR following treatment with a combination therapy according to the methods provided herein. In one embodiment provided herein a patient is diagnosed having a PR following treatment with a combination therapy according to the methods provided herein. In one embodiment provided herein a patient is diagnosed having SD following treatment with a combination therapy according to the methods provided herein.

In one embodiment of the methods described herein, a patient has been treated with one or more cancer therapies before administration of a combination therapy described herein. In one embodiment of the methods described herein, the prior therapy comprises fulvestrant and/or a CDK4/6 inhibitor (e.g. palbociclib, ribociclib, or abemaciclib). In another embodiment, a patient described herein has not been prior treated with fulvestrant, an AKT inhibitor, and/or a CDK4/6 inhibitor.

In one embodiment of the methods described herein, a patient has breast cancer described herein that is resistant to one or more cancer therapies. In one embodiment of the methods described herein, resistance to cancer therapy includes recurrence of cancer or refractory cancer. Recurrence may refer to the reappearance of cancer, in the original site or a new site, after treatment. In one embodiment of the methods described herein, resistance to a cancer therapy includes progression of the cancer during treatment with the anti-cancer therapy. In some embodiments of the methods described herein, resistance to a cancer therapy includes cancer that does not response to treatment. The cancer may be resistant at the beginning of treatment or it may become resistant during treatment. In some embodiments of the methods described herein, the cancer is at early stage or at late stage.

In one embodiment, a patient described herein has been pretreated with an aromatase inhibitor or tamoxifen prior to administration of the combination therapy described herein. In one such embodiment, the patient relapsed during prior treatment with an aromatase inhibitor or tamoxifen or otherwise demonstrated disease progression after such administration. In one such embodiment, the relapse or disease progression was observed during the first 12 months of a 1L endocrine therapy. In one embodiment, the prior treatment was with one or more aromatase inhibitors as described herein. In another embodiment, the prior treatment was with tamoxifen. In still another such embodiment, the prior treatment was for locally advanced unresectable or metastatic breast cancer. In one such embodiment, a patient described herein has been pretreated with letrozole, tamoxifen, anastrozole, or exemestane. In another such embodiment, a patient described herein has been treated for 3-6 years with an aromatase inhibitor or tamoxifen prior to administration of a combination therapy described herein. In another such embodiment, a patient described herein has been treated for greater than 6 years with an aromatase inhibitor or tamoxifen prior to administration of a combination therapy described herein. In still another embodiment, a patient herein is post-menopausal. In another embodiment, a patient herein has at least one measurable lesion as measured by, for example, RECIST.

In one embodiment of the methods described herein, a patient having hormone receptor positive and HER2 negative locally advanced unresectable or metastatic breast cancer as described herein may have undergone surgical treatment such as, for example, surgery that is breast-conserving (i.e., a lumpectomy, which focuses on removing the primary tumor with a margin), or more extensive (i.e., mastectomy, which aims for complete removal of all of the breast tissue) prior to administration of a combination therapy described herein. In another embodiment, a patient described herein may undergo surgical treatment following treatment with a combination therapy described herein.

Radiation therapy is typically administered post-surgery to the breast/chest wall and/or regional lymph nodes, with the goal of killing microscopic cancer cells left post-surgery. In the case of a breast conserving surgery, radiation is administered to the remaining breast tissue and sometimes to the regional lymph nodes (including axillary lymph nodes). In the case of a mastectomy, radiation may still be administered if factors that predict higher risk of local recurrence are present. In some embodiments of the methods provided herein a patient having hormone receptor positive and HER2 negative locally advanced unresectable or metastatic breast cancer as described herein may have received radiation therapy prior to administration of a combination therapy described herein. In other embodiments of the methods provided herein a patient having hormone receptor positive and HER2 negative locally advanced unresectable or metastatic breast cancer as described herein may have received radiation therapy following administration of a combination therapy described herein.

In another embodiment, the patient has not been pretreated with a PI3K inhibitor. In still another embodiment, the patient has not been pretreated with a mTOR inhibitor. In still another embodiment, the patient has not been pretreated with an AKT inhibitor. In yet another embodiment, the patient has not been previously treated with a cytotoxic chemotherapy regimen for metastatic breast cancer. In still another embodiment, a patient described herein has not been previously treated with a SERD (selective estrogen receptor degrader), including for example, fulvestrant.

In another aspect provided herein is use of a combination therapy comprising ipatasertib, fulvestrant, and a CDK4/6 inhibitor (e.g. palbociclib, ribociclib, or abemaciclib) in the manufacture of a medicament for treating hormone receptor positive and HER2 negative locally advanced unresectable breast cancer or metastatic breast cancer. Such combination therapies can further comprise dosing and regimens as set forth herein.

In another aspect provided herein is a combination therapy comprising ipatasertib, fulvestrant, and a CDK4/6 inhibitor (e.g. palbociclib, ribociclib, or abemaciclib) for use in the treatment of hormone receptor positive and HER2 negative locally advanced unresectable breast cancer or metastatic breast cancer. Such combination therapies can further comprise dosing and regimens as set forth herein.

Also provided herein is use of a combination therapy comprising ipatasertib, fulvestrant, and a CDK4/6 inhibitor (e.g. palbociclib, ribociclib, or abemaciclib) in the manufacture of a medicament for treating hormone receptor positive and HER2 negative locally advanced unresectable breast cancer or metastatic breast cancer. In another embodiment, is a use of a combination therapy comprising ipatasertib, fulvestrant, and palbociclib in the manufacture of a medicament for treating hormone receptor positive and HER2 negative locally advanced unresectable breast cancer or metastatic breast cancer. In one such embodiment, is a use of a combination therapy comprising ipatasertib, fulvestrant, and palbociclib in the manufacture of a medicament for treating hormone receptor positive and HER2 negative locally advanced unresectable breast cancer. In another such embodiment, is a use of a combination therapy comprising ipatasertib, fulvestrant, and palbociclib in the manufacture of a medicament for treating hormone receptor positive and HER2 negative metastatic breast cancer. Such combination therapies can further comprise dosing and regimens as set forth herein.

Also provided herein is a combination therapy comprising ipatasertib, fulvestrant, and a CDK4/6 inhibitor (e.g. palbociclib, ribociclib, or abemaciclib) for use in the treatment of hormone receptor positive and HER2 negative locally advanced unresectable breast cancer or metastatic breast cancer. In another embodiment, is a combination therapy comprising ipatasertib, fulvestrant, and palbociclib for use in the treatment of hormone receptor positive and HER2 negative locally advanced unresectable breast cancer or metastatic breast cancer. In one such embodiment, is a combination therapy comprising ipatasertib, fulvestrant, and palbociclib for use in the treatment of hormone receptor positive and HER2 negative locally advanced unresectable breast cancer. In another such embodiment, is a combination therapy comprising ipatasertib, fulvestrant, and palbociclib use in the treatment of hormone receptor positive and HER2 negative metastatic breast cancer. Such combination therapies can further comprise dosing and regimens as set forth herein.

Also provided herein are methods of inhibiting tumor growth or producing tumor regression in a patient described herein by administering a combination therapy described herein.

In one embodiment provided herein is a method of producing or improving tumor regression in a patient described herein by administering a combination therapy described herein.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. ipatasertib, fulvestrant, and palbociclib) is administered in a dosing regimen comprising a staggered dosing schedule. In one embodiment, the combination therapy described herein (e.g. ipatasertib, fulvestrant, and palbociclib) is administered simultaneously on a 28-day cycle.

In one embodiment of the methods provided herein, ipatasertib and palbociclib are each individually administered QD on days 1-21 of each 28-day cycle. In such embodiments, fulvestrant is administered as described herein such as on day 1 and 15 of the first 28-day cycle and day 1 of each 28-day cycle thereafter.

In one method of administering the combination therapy described herein, the method comprises administering to a patient having locally advanced unresectable or metastatic breast cancer a dosing regimen comprising:
　(a) ipatasertib QD at a dose described herein on days 1-21 of a first 28-day cycle;
　(b) palbociclib QD at a dose described herein on days 1-21 of a first 28-day cycle; and
　(c) fulvestrant at a dose described herein on days 1 and 15 of a first 28-day cycle.

In one embodiment of such methods, the first 28-day cycle is preceded by a 5-7 day run in period, as provided herein, comprising QD administration of ipatasertib prior to day 1 of the first 28-day cycle. In another embodiment of such methods, the first 28-day cycle is proceeded by a rest period comprising at least 7 days.

In another aspect provided herein is use of a combination therapy comprising:
　(a) ipatasertib QD at a dose described herein on days 1-21 of a first 28-day cycle;
　(b) palbociclib QD at a dose described herein on days 1-21 of a first 28-day cycle; and
　(c) fulvestrant at a dose described herein on days 1 and 15 of a first 28-day cycle in the manufacture of a medicament comprising a dosing regimen comprising for treating hormone receptor positive and HER2 negative locally advanced unresectable breast cancer or metastatic breast cancer.

In another aspect provided herein is a combination therapy comprising:
　(a) ipatasertib QD at a dose described herein on days 1-21 of a first 28-day cycle;
　(b) palbociclib QD at a dose described herein on days 1-21 of a first 28-day cycle; and
　(c) fulvestrant at a dose described herein on days 1 and 15 of a first 28-day cycle for use in the treatment of hormone receptor positive and HER2 negative locally advanced unresectable breast cancer or metastatic breast cancer.

In another embodiment of such methods, the dosing regimen further comprises administration of one or more additional 28-day cycles comprising administration of:
　(a) ipatasertib at a dose described herein on days 1-21 of each additional 28-day cycle;
　(b) palbociclib at a dose described herein on days 1-21 of each additional 28-day cycle; and
　(c) fulvestrant at a dose described herein on day 1 of each additional 28-day cycle.

In one embodiment, each additional 28-day cycle includes a rest period comprising at least 7 days prior to commencing the next cycle. In another such embodiment, ipatasertib is administered at an amount of 300 mg.

In another method of administering a combination therapy described herein, the method comprises administering to a patient having locally advanced unresectable or metastatic breast cancer a dosing regimen comprising:
(a) ipatasertib QD at a dose described herein on days 1-21 of a first 28-day cycle; and
(b) palbociclib QD at a dose described herein on days 1-21 of a first 28-day cycle.

In another method of administering a combination therapy described herein, the method comprises administering to a patient having locally advanced unresectable or metastatic breast cancer a dosing regimen comprising:
(a) ipatasertib QD at a dose described herein on days 1-21 of a first 28-day cycle; and
(b) fulvestrant at a dose described herein on days 1 and 15 of a first 28-day cycle.

In another embodiment of the methods described herein, the dosing reduces the number or frequency of grade 2 or grade 3 or higher grade adverse event comparable to administration of either agent alone.

In one embodiment, the patient is at least 18 years old. In one embodiment, the patient does not have a history of Type I or Type II diabetes mellitus requiring insulin. In another embodiment, the patient does not have a history of inflammatory bowel disease or active bowel inflammation. In still another embodiment, the patient does not have a lung disease including, for example, pneumonitis, interstitial lung disease, idiopathic pulmonary fibrosis, cystic fibrosis, Aspergillosis, or active tuberculosis. In still another embodiment, the patient does not have a history of opportunistic infections (including opportunistic lung infections).

Breast cancer is a heterogeneous disease with many distinct subtypes as defined by molecular signatures and a diverse array of mutational profiles. In one embodiment, a patient can be tested for PIK3CA/AKT1/PTEN-alteration status. In one embodiment, a patient described herein can be tested for one or more of a phosphatase and tensin homolog (PTEN) mutation, PTEN loss (or loss of PTEN function), a phosphatidylinositol-4,5-bisphosphate 3-kinase catalytic subunit alpha (PIK3CA) mutation, a protein kinase B alpha (AKT1) mutation, or a combination thereof. In one embodiment, the PTEN loss is hemizygous or homozygous. In another embodiment, samples of patients described herein can be assessed for additional biomarkers in an effort to identify factors that may correlate with the safety and efficacy of the study treatments.

In one embodiment of the methods described herein, NGS, whole genome sequencing (WGS), other methods, or a combination thereof can be used for DNA obtained from blood samples and tumor tissue from patients described herein. Such samples may be analyzed to identify germline (e.g., BRCA1/2) and somatic alterations that are predictive of response to study drug, are associated with progression to a more severe disease state, are associated with acquired resistance to study drug, or can increase the knowledge and understanding of disease biology. In another embodiment of the methods described herein, patients described herein can have cancer characterized by activation of PI3K/Akt signaling such as activating mutations in PIK3CA or AKT1 as well as through alterations in PTEN, such as those provided herein. In another embodiment, PIK3CA/AKT1/PTEN-altered tumor status will be determined using an NGS assay (e.g., Foundation Medicine, Inc. [FMI]). Review of PIK3CA/AKT1/PTEN-altered status in archival tissue and response measures can be performed on an ongoing basis. Expression of biomarkers (e.g. PTEN) as provided herein can be measured using techniques known in the art such as, for example, immunohistochemistry (IHC).

Circulating tumor DNA (ctDNA) can be detected in the blood of cancer patients with epithelial cancers and may have diagnostic and therapeutic significance (Schwarzenbach et al. 2011). For example, the mutational status of tumor cells may be obtained through the isolation of ctDNA (Maheswaran S, et al. N Engl J Med 2008; 359:366-77), and ctDNA has been used to monitor treatment effectiveness in melanoma (Shinozaki M, et al. Clin Cancer Res 2007; 13:2068-74). Blood samples from patients described herein can be collected at screening, at time of first tumor assessment, and/or at the study completion/early termination visit. In one embodiment, the samples are used to evaluate oncogenic genetic alterations at baseline and to assess for the possible emergence of new alteration after treatment with ipatasertib, fulvestrant, and a CDK4/6 inhibitor (e.g. palbociclib, ribociclib, or abemaciclib).

Provided below are exemplary embodiments of the invention herein.

Embodiment No 1. A method of treating hormone receptor positive and HER2 negative locally advanced unresectable or metastatic breast cancer in a patient having hormone receptor positive and HER2 negative locally advanced unresectable or metastatic breast cancer, the method comprising administering to the patient a combination therapy comprising: (i) ipatasertib; (ii) fulvestrant; and (iii) a CDK4/6 inhibitor, wherein said combination therapy is administered over a 28-day cycle.

Embodiment No 2. A method of treating hormone receptor positive and HER2 negative locally advanced unresectable or metastatic breast cancer in a patient having hormone receptor positive and HER2 negative locally advanced unresectable or metastatic breast cancer, the method comprising administering to the patient a combination therapy comprising: (i) ipatasertib; (ii) fulvestrant; and (iii) palbociclib, wherein said combination therapy is administered over a 28-day cycle.

Embodiment No 3. A method of treating hormone receptor positive and HER2 negative locally advanced unresectable or metastatic breast cancer in a patient having hormone receptor positive and HER2 negative locally advanced unresectable or metastatic breast cancer, the method comprising administering to the patient a combination therapy comprising a dosing regimen comprising: (a) administering ipatasertib QD on days 1-21 of a first 28-day cycle; (b) administering palbociclib QD on days 1-21 of a first 28-day cycle; and (c) administering fulvestrant on days 1 and 15 of a first 28-day cycle.

Embodiment No 4. The method of any one of embodiments 1-3, further comprising administering ipatasertib alone for at least a 5-7 day run in period prior to day 1 of the first 28-day cycle.

Embodiment No 5. The method of any one of embodiments 1-4, further comprising a rest period comprising at least 7 days.

Embodiment No 6. The method of any one of embodiments 1-5, further comprising one or more additional 28-day cycles comprising: (a) administering ipatasertib on days 1-21 of each additional 28-day cycle; (b) administering palbociclib on days 1-21 of each additional 28-day cycle; and (c) administering fulvestrant on day 1 of each additional 28-day cycle.

Embodiment No 7. The method of any one of embodiments 1-6, wherein ipatasertib is administered at an amount of 300 mg.

Embodiment No 8. The method of any one of embodiments 1-7 wherein fulvestrant is administered at an amount of 500 mg by intravenous (IV) infusion.

Embodiment No 9. A method of inhibiting tumor growth or producing/increasing tumor regression in a patient having hormone receptor positive and HER2 negative locally advanced unresectable or metastatic breast cancer, the method comprising administering to the patient a combination therapy according to the methods of any one of embodiments 1-8.

Embodiment No 10. The method of any one of embodiments 1-9, wherein said patient has hormone receptor positive and HER2 negative locally advanced unresectable or metastatic breast cancer determined to have a phosphatase and tensin homolog (PTEN) mutation, PTEN loss, a phosphatidylinositol-4,5-bisphosphate 3-kinase catalytic subunit alpha (PIK3CA) mutation, a protein kinase B alpha (AKT1) mutation, or a combination thereof.

Embodiment No 11. The method of embodiment 10, wherein the PTEN loss expression is hemizygous or homozygous.

Embodiment No 12. The method of any one of embodiments 1-11, wherein the patient has locally advanced unresectable or metastatic breast cancer and has relapsed during adjuvant endocrine therapy or has disease progression during the initial 12-months of 1L endocrine therapy.

Embodiment No 13. The method of any one of embodiments 1-12, wherein the patient described herein has been pretreated with an aromatase inhibitor or tamoxifen prior to administration of the combination therapy.

Embodiment No 14. The method of any one of embodiments 1-13, wherein the patient has been pretreated with one or more of letrozole, tamoxifen, anastrozole, or exemestane.

Embodiment No 15. The method of any one of embodiments 1-14, wherein the patient is post-menopausal.

Embodiment No 16. The method of any one of embodiments 1-15, wherein the patient has not been pretreated with a PI3K inhibitor, a mTOR inhibitor, an AKT inhibitor or a SERD (selective estrogen receptor degrader).

Embodiment No 17. The method of any one of embodiments 1-16, wherein the patient does not have a history of Type I or Type II diabetes mellitus requiring insulin.

Embodiment No 18. The method of any one of embodiments 1-17, wherein the patient does not have a history of inflammatory bowel disease or active bowel inflammation.

Embodiment No 19. The method of any one of embodiments 1-18, wherein the patient does not have a lung disease selected from the group consisting of, pneumonitis, interstitial lung disease, idiopathic pulmonary fibrosis, cystic fibrosis, Aspergillosis, and active tuberculosis.

Embodiment No 20. A method of treating hormone receptor positive and HER2 negative locally advanced unresectable or metastatic breast cancer in a patient having hormone receptor positive and HER2 negative locally advanced unresectable or metastatic breast cancer, the method comprising administering to the patient a combination therapy comprising: (i) ipatasertib; and (ii) fulvestrant, wherein said combination therapy is administered over a 28-day cycle Embodiment No 21. Use of a combination therapy comprising ipatasertib, fulvestrant, and a CDK4/6 inhibitor (e.g. palbociclib, ribociclib, or abemaciclib) in the manufacture of a medicament for treating hormone receptor positive and HER2 negative locally advanced unresectable breast cancer or metastatic breast cancer.

Embodiment No 22. Use of a combination therapy comprising ipatasertib, fulvestrant, and palbociclib in the manufacture of a medicament for treating hormone receptor positive and HER2 negative locally advanced unresectable breast cancer or metastatic breast cancer.

Embodiment No 23. Use of a combination therapy comprising ipatasertib, fulvestrant, and a CDK4/6 inhibitor (e.g. palbociclib, ribociclib, or abemaciclib) and a dosing regimen as set forth herein in the manufacture of a medicament for treating hormone receptor positive and HER2 negative locally advanced unresectable breast cancer or metastatic breast cancer.

Embodiment No 24. Use of a combination therapy comprising a dosing regimen comprising: (a) administering ipatasertib QD on days 1-21 of a first 28-day cycle; (b) administering palbociclib QD on days 1-21 of a first 28-day cycle; and (c) administering fulvestrant on days 1 and 15 of a first 28-day cycle in the manufacture of a medicament for treating hormone receptor positive and HER2 negative locally advanced unresectable breast cancer or metastatic breast cancer.

Embodiment No 25. The use of any one of embodiments 21-24, wherein the medicament is for treating hormone receptor positive and HER2 negative locally advanced unresectable breast cancer.

Embodiment No 26. The use of any one of embodiments 21-24, wherein the medicament is for treating hormone receptor positive and HER2 negative metastatic breast cancer.

Embodiment No 27. A combination therapy comprising ipatasertib, fulvestrant, and a CDK4/6 inhibitor (e.g. palbociclib, ribociclib, or abemaciclib) for use in the treatment of hormone receptor positive and HER2 negative locally advanced unresectable breast cancer or metastatic breast cancer.

Embodiment No 28. A combination therapy comprising ipatasertib, fulvestrant, and palbociclib for use in the treatment of hormone receptor positive and HER2 negative locally advanced unresectable breast cancer or metastatic breast cancer.

Embodiment No 29. A combination therapy comprising ipatasertib, fulvestrant, and a CDK4/6 inhibitor (e.g. palbociclib, ribociclib, or abemaciclib) and a dosing regimen as set forth herein for use in the treatment of hormone receptor positive and HER2 negative locally advanced unresectable breast cancer or metastatic breast cancer.

Embodiment No 30. A combination therapy comprising a dosing regimen comprising: (a) administering ipatasertib QD on days 1-21 of a first 28-day cycle; (b) administering palbociclib QD on days 1-21 of a first 28-day cycle; and (c) administering fulvestrant on days 1 and 15 of a first 28-day cycle for use in the treatment of hormone receptor positive and HER2 negative locally advanced unresectable breast cancer or metastatic breast cancer.

Embodiment No 31. The combination of any one of embodiments 27-30, for use in the treatment of hormone receptor positive and HER2 negative locally advanced unresectable breast cancer.

Embodiment No 32. The combination of any one of embodiments 27-30, for use in the treatment of hormone receptor positive and HER2 negative metastatic breast cancer.

Examples

Figure 7A:
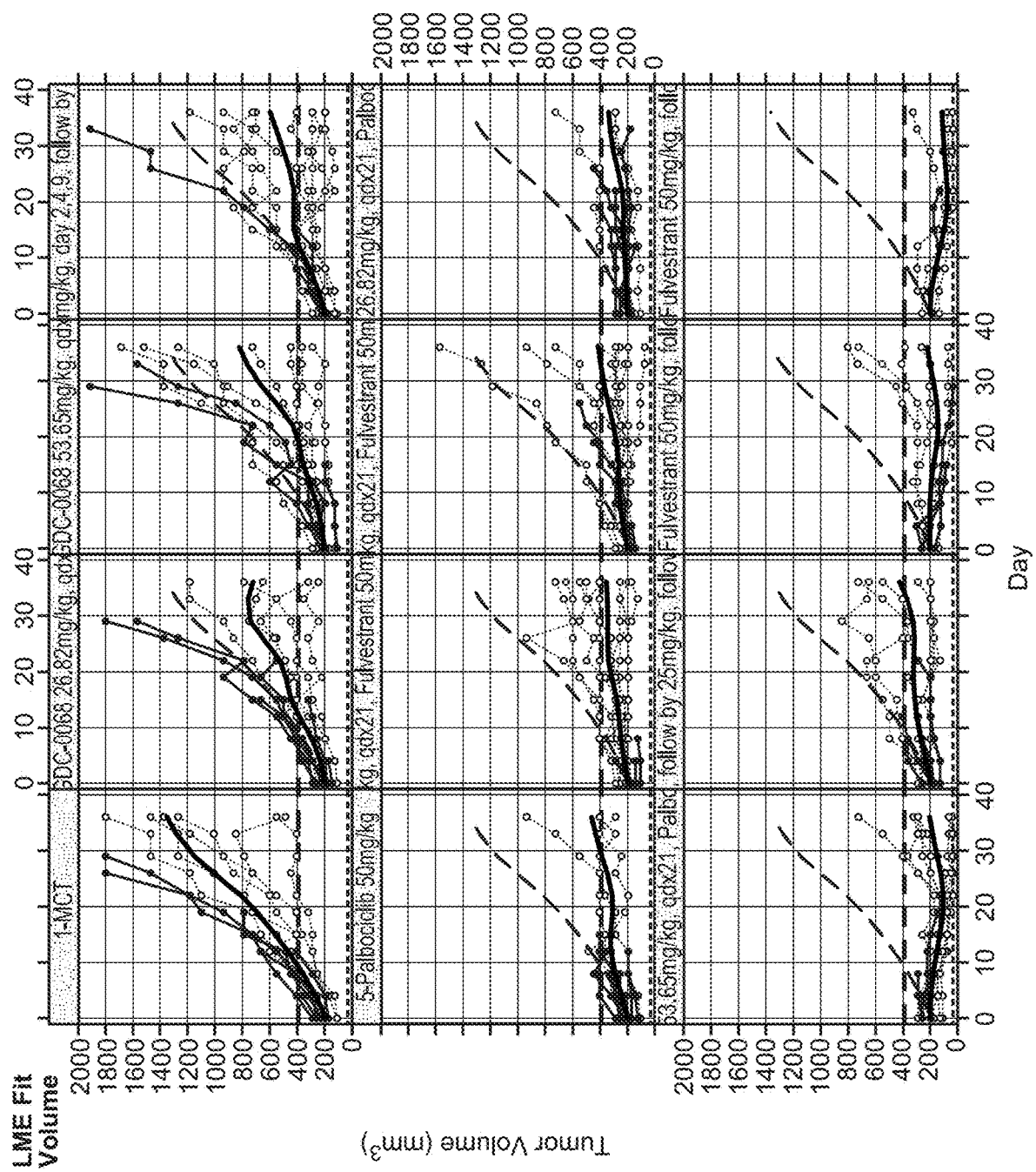
FIG. 7A and FIG. 7B show durable responses with treatment with ipatasertib, fulvestrant, and palbociclib as regrowth of Ipatasertib with Palbociclib and Fulvestrant in the MCF-7 (CRL) Breast Cancer Model.
Figure 7B:
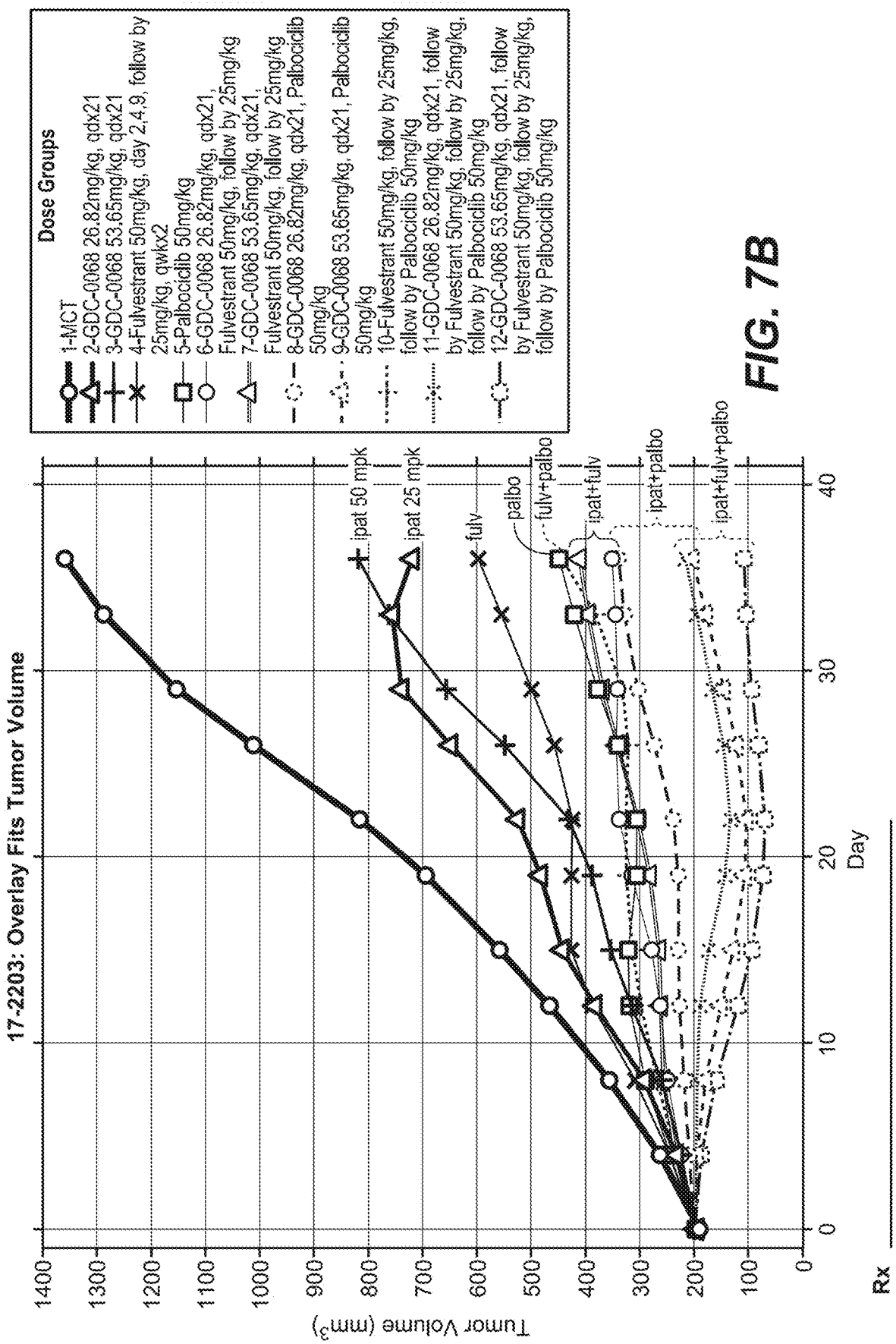
Figure 8A:
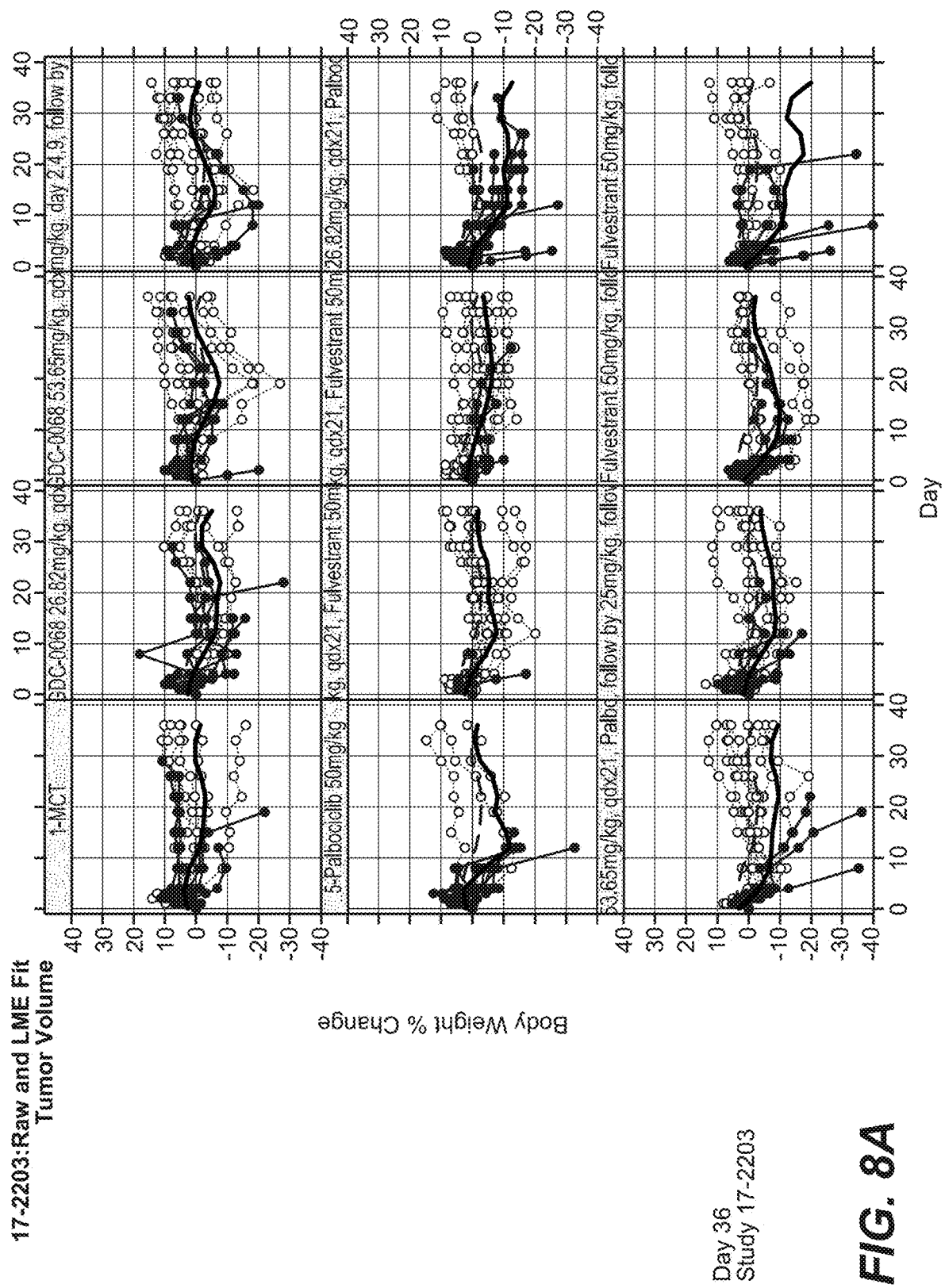
FIG. 8A and FIG. 8B show % BW Loss of Ipatasertib with and Palbociclib and Fulvestrant in the MCF-7 (CRL) Breast Cancer Model.
Figure 8B:
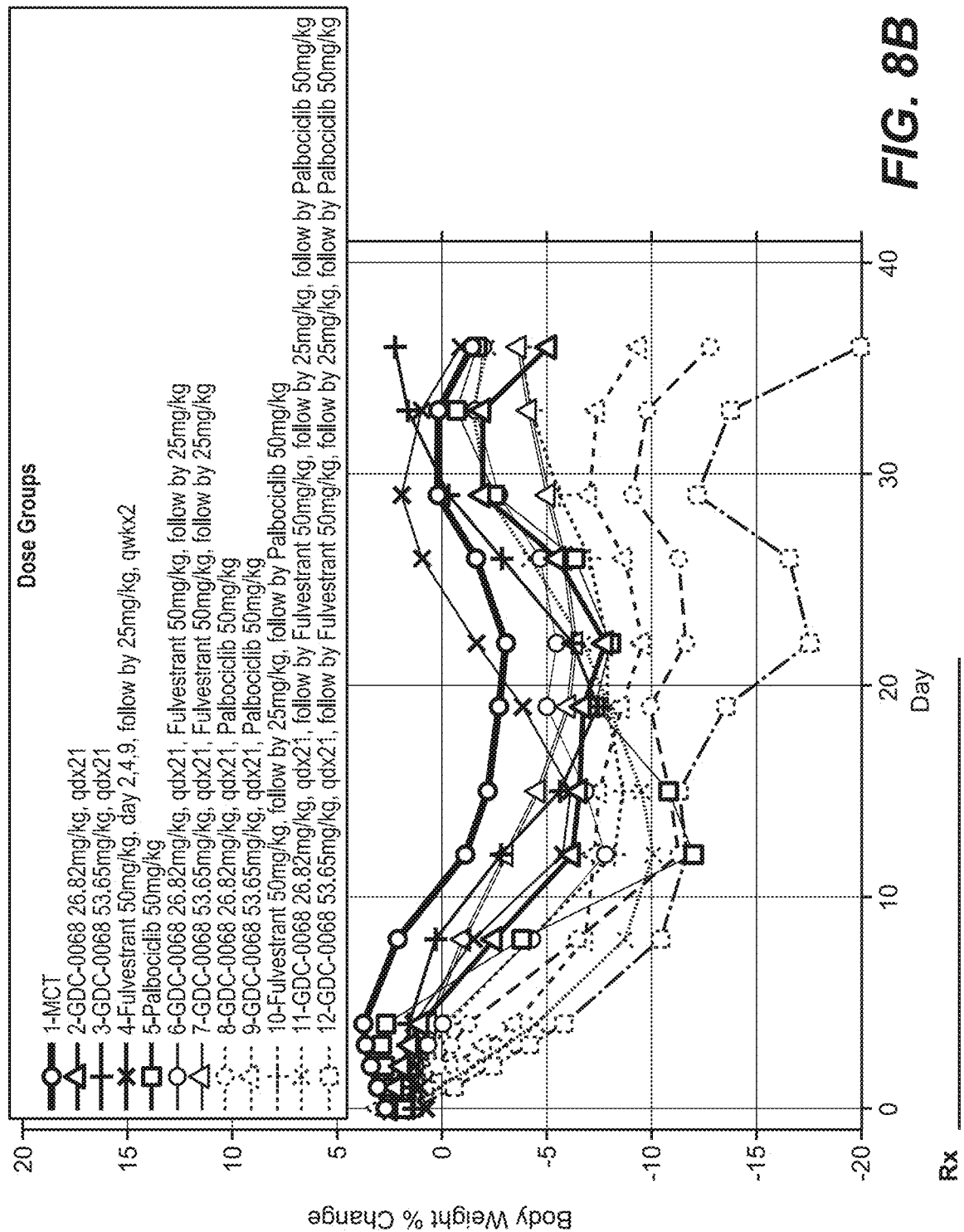

Cell lines were treated with agents described herein (e.g. ipatasertib, palbociclib, and fulvestrant). Breast cancer cell lines appeared to show differential single agent sensitivity to ipatasertib and palbociclib. (See FIG. 1A and FIG. 1B). There was synergy between ipatasertib and palbociclib as show by the BLISS scores of FIGS. 2A, 2B, 2C, and 2D. Synergistic effect was seen between the triplet combo described herein as shown by FIGS. 3A, 3B, 4A, 4B, 5A, and 5B. Comparable effects of treatment with doublets is shown in FIGS. 6A, 6B, 6C, 6D, 6E, and 6F. Durable responses were seen in the triplet combo described herein following 21 days of dosing as shown by FIGS. 7A and 7B. The percent weight loss resulting from treatment is shown by FIGS. 8A and 8B.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating hormone receptor positive and HER2 negative locally advanced unresectable or metastatic breast cancer in a patient having hormone receptor positive and HER2 negative locally advanced unresectable or metastatic breast cancer, the method comprising administering to the patient a combination therapy comprising:
   (i) ipatasertib; and
   (ii) fulvestrant,
   wherein said combination therapy is administered over a 28-day cycle; and
   wherein the patient has previously been treated with a CDK4/6 inhibitor.

2. The method of claim 1, wherein the method is for treating hormone receptor positive and HER2 negative locally advanced unresectable breast cancer.

3. The method of claim 1, wherein the method is for treating hormone receptor positive and HER2 negative metastatic breast cancer.

4. The method of claim 1, comprising administering about 400 mg ipatasertib once per day.

5. The method of claim 4, comprising orally administering ipatasertib.

6. The method of claim 1, comprising administering about 500 mg fulvestrant.

7. The method of claim 6, comprising intramuscularly administering fulvestrant.

8. The method of claim 1, comprising administering:
   (a) about 400 mg ipatasertib once per day on days 1-21 of a first 28-day cycle; and
   (b) about 500 mg fulvestrant on days 1 and 15 of the first 28-day cycle.

9. The method of claim 8, comprising administering:
   (a) about 400 mg ipatasertib once per day on days 1-21 of each additional 28-day cycle; and
   (b) about 500 mg fulvestrant on day 1 of each additional 28-day cycle.

10. The method of claim 1, wherein the patient has been previously treated with an aromatase inhibitor or tamoxifen prior to administration of ipatasertib and fulvestrant.

11. The method of claim 10, wherein the patient has been previously treated with an aromatase inhibitor prior to administration of ipatasertib and fulvestrant.

12. The method of claim 1, wherein the CDK4/6 inhibitor is palbociclib, ribociclib, or abemaciclib.

13. The method of claim 1, wherein the patient has previously been treated with an aromatase inhibitor.

14. The method of claim 13, wherein the patient has disease progression during or after the previous treatment with the aromatase inhibitor.

15. The method of claim 1, wherein the patient has not been previously treated with a PI3K inhibitor, a mTOR inhibitor, an AKT inhibitor, or a selective estrogen receptor degrader.

16. The method of claim 1, wherein the patient does not have a history of:
   (a) Type I or Type II diabetes mellitus requiring insulin;
   (b) inflammatory bowel disease or active bowel inflammation; or
   (c) Type I or Type II diabetes mellitus requiring insulin and inflammatory bowel disease or active bowel inflammation.

17. The method of claim 1, wherein the ipatasertib is a monohydrochloride salt.

18. The method of claim 17, wherein the ipatasertib is an amorphous monohydrochloride salt.

19. The method of claim 1, wherein the patient has disease progression during or after the previous treatment with the CDK4/6 inhibitor.

* * * * *